United States Patent
Takahashi et al.

(10) Patent No.: US 12,417,626 B2
(45) Date of Patent: *Sep. 16, 2025

(54) INFORMATION PROCESSING DEVICE, DISPLAY METHOD, AND NON-TRANSITORY COMPUTER-READABLE MEDIUM FOR SUPPORTING MEDICAL DECISION MAKING

(71) Applicant: NEC Corporation, Tokyo (JP)

(72) Inventors: Ikuma Takahashi, Tokyo (JP); Tatsu Kimura, Tokyo (JP); Kimiyasu Takoh, Tokyo (JP); Kenichi Kamijo, Tokyo (JP); Hiroyasu Saiga, Tokyo (JP); Shota Ohtsuka, Tokyo (JP); Motoyasu Okutsu, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/544,539

(22) Filed: Dec. 19, 2023

(65) Prior Publication Data
US 2024/0119727 A1 Apr. 11, 2024

Related U.S. Application Data

(63) Continuation of application No. 17/637,141, filed as application No. PCT/JP2020/014537 on Mar. 30, 2020, now Pat. No. 12,080,059.

(51) Int. Cl.
*A61B 1/00* (2006.01)
*G06T 7/00* (2017.01)
(Continued)

(52) U.S. Cl.
CPC ........ *G06V 10/987* (2022.01); *A61B 1/00006* (2013.01); *A61B 1/00009* (2013.01);
(Continued)

(58) Field of Classification Search
CPC ................................ G06V 10/987; A61B 1/00
See application file for complete search history.

(56) References Cited

U.S. PATENT DOCUMENTS

| 2004/0225223 A1 | 11/2004 | Honda et al. |
| 2006/0050943 A1 | 3/2006 | Ozaki et al. |

(Continued)

FOREIGN PATENT DOCUMENTS

| JP | 2000-276587 A | 10/2000 |
| JP | 2004-180932 A | 7/2004 |

(Continued)

OTHER PUBLICATIONS

US Office Action for U.S. Appl. No. 17/637,141, mailed on Jan. 24, 2024.

(Continued)

*Primary Examiner* — Yi Yang
(74) *Attorney, Agent, or Firm* — Sughrue Mion, PLLC

(57) ABSTRACT

An information processing device includes: a first acquisition unit configured to acquire a capturing time of a lesion image instructed to be saved by a user, from a series of images captured by an endoscope during examination with the endoscope; a second acquisition unit configured to acquire a capturing time of a lesion image detected by detection processing for the series of images captured by the endoscope during the examination; and a display control unit configured to cause a display device to display a first capturing time and a second capturing time which are plotted on a time axis, the first capturing time being the capturing time acquired by the first acquisition unit, the second capturing time being the capturing time acquired by the second acquisition unit.

10 Claims, 18 Drawing Sheets

(51) Int. Cl.
  *G06T 11/20* (2006.01)
  *G06V 10/98* (2022.01)

(52) U.S. Cl.
  CPC ........ *A61B 1/0005* (2013.01); *A61B 1/00055* (2013.01); *G06T 7/0016* (2013.01); *G06T 11/206* (2013.01); *A61B 1/0004* (2022.02); *G06T 2200/24* (2013.01); *G06T 2207/10068* (2013.01); *G06T 2207/20092* (2013.01); *G06T 2207/30096* (2013.01); *G06V 2201/03* (2022.01)

(56) References Cited

U.S. PATENT DOCUMENTS

| | | |
|---|---|---|
| 2007/0036415 A1 | 2/2007 | Takeo |
| 2009/0054755 A1 | 2/2009 | Shilbashi ............... G16H 15/00 600/407 |
| 2012/0316421 A1 | 12/2012 | Kumar et al. |
| 2013/0184537 A1 | 7/2013 | Konuma ................ A61B 6/586 600/300 |
| 2016/0216150 A1 | 7/2016 | Groeber .................. A61M 1/28 |
| 2017/0004620 A1 | 1/2017 | Kitamura .................. G06T 7/90 |
| 2019/0125173 A1 | 5/2019 | Lee et al. |
| 2019/0374088 A1 | 12/2019 | Watanabe ............ A61B 1/0052 |
| 2020/0058384 A1 | 2/2020 | Sugai ..................... G16H 10/60 |
| 2020/0126223 A1 | 4/2020 | Kitamura et al. |

FOREIGN PATENT DOCUMENTS

| | | |
|---|---|---|
| JP | 2006-061469 A | 3/2006 |
| JP | 2007-307396 A | 11/2007 |
| WO | 2018/159363 A1 | 9/2018 |
| WO | 2018/198327 A1 | 11/2018 |
| WO | 2018/216617 A1 | 11/2018 |
| WO | 2019/088008 A1 | 5/2019 |

OTHER PUBLICATIONS

International Search Report for PCT Application No. PCT/JP2020/014537, mailed on Jun. 16, 2020.
Japanese Office Action for JP Application No. 2022-512893, mailed on Aug. 9, 2022 with English Translation.
Extended European Search Report for EP Application No. 20928911.5, dated on Apr. 24, 2023.

INFORMATION PROCESSING DEVICE, DISPLAY METHOD, AND NON-TRANSITORY COMPUTER-READABLE MEDIUM FOR SUPPORTING MEDICAL DECISION MAKING

This application is a Continuation of U.S. application Ser. No. 17/637,141 filed on Feb. 22, 2022, which is a National Stage Entry of PCT/JP2020/014537 filed on Mar. 30, 2020, the contents of all of which are incorporated herein by reference, in their entirety.

TECHNICAL FIELD

The present disclosure relates to an information processing device, a display method, and a non-transitory computer-readable medium for storing a program.

BACKGROUND ART

A system is known that supports medical treatment using an endoscope. For example, Patent Literature 1 discloses an image display device that displays an image captured by a capsule-type endoscope. In the image display device, when an operation of selecting an "Auto" icon is performed, an image of a bleeding site is automatically extracted.

CITATION LIST

Patent Literature

Patent Literature 1: Japanese Unexamined Patent Application Publication No 2006-061469

SUMMARY OF INVENTION

Technical Problem

In a case of detection of a lesion by detection processing on an image captured by an endoscope in real time in addition to detection of a lesion by a user (for example, a doctor) during in-vivo examination using an endoscope, there may be discrepancy between the detection result by the user and the detection result by the detection processing. However, it is difficult to easily recognize such discrepancy. On the other hand, in the technique disclosed in Patent Literature 1, only an image of a bleeding site is automatically extracted, and the comparison between the automatic extraction result and the detection result by the user is not considered.

The present disclosure has been made in order to solve such a problem, and is to provide an information processing device, a display method, and a program which enable easy recognition of the discrepancy between the detection result by detection processing for an image captured by an endoscope and the detection result by a user.

Solution to Problem

An information processing device according to a first aspect of the present disclosure includes:
- a first acquisition unit configured to acquire a capturing time of a lesion image instructed to be saved by a user, from a series of images captured by an endoscope during examination with the endoscope;
- a second acquisition unit configured to acquire a capturing time of a lesion image detected by detection processing for the series of images captured by the endoscope during the examination; and
- a display control unit configured to cause a display device to display a first capturing time and a second capturing time which are plotted on a time axis, the first capturing time being the capturing time acquired by the first acquisition unit, the second capturing time being the capturing time acquired by the second acquisition unit.

A display method according to a second aspect of the present disclosure includes:
- acquiring a capturing time of a lesion image instructed to be saved by a user, from a series of images captured by an endoscope during examination with the endoscope;
- acquiring a capturing time of a lesion image detected by detection processing for the series of images captured by the endoscope during the examination; and
- causing a display device to display a first capturing time and a second capturing time which are plotted on a time axis, the first capturing time being the capturing time of the lesion image instructed to be saved by the user, the second capturing time being the capturing time of the lesion image detected by the detection processing.

A program according to a third aspect of the present disclosure causes a computer to execute:
- a first acquisition step of acquiring a capturing time of a lesion image instructed to be saved by a user, from a series of images captured by an endoscope during examination with the endoscope;
- a second acquisition step of acquiring a capturing time of a lesion image detected by detection processing for the series of images captured by the endoscope during the examination; and
- a display control step of causing a display device to display a first capturing time and a second capturing time which are plotted on a time axis, the first capturing time being the capturing time acquired in the first acquisition step, the second capturing time being the capturing time acquired in the second acquisition step.

Advantageous Effect of Invention

According to the present disclosure, it is possible to provide an information processing device, a display method, and a program which enable easy recognition of the discrepancy between the detection result by detection processing for an image captured by an endoscope and the detection result by a user.

DESCRIPTION OF EMBODIMENTS

Figure 1:
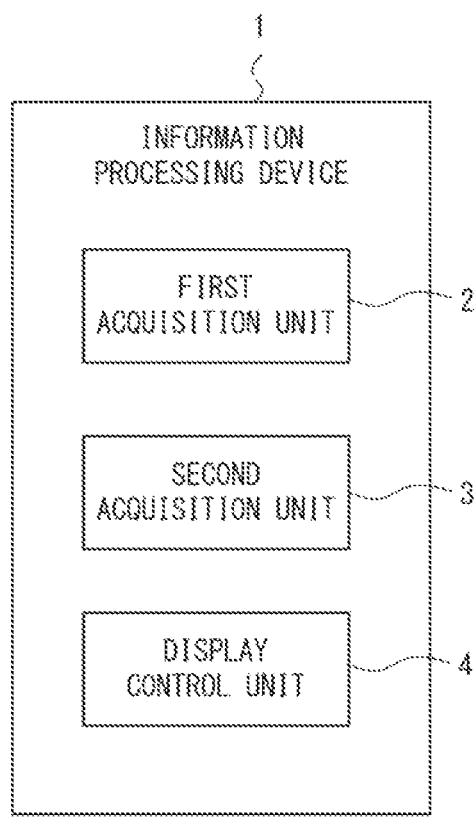
FIG. 1 is a block diagram showing an example of a configuration of an information processing device according to a first example embodiment.

For clarifying the explanation, the following descriptions and the drawings are omitted and simplified as appropriate. In each drawing, the same or corresponding components are designated by the same reference numerals, and duplicate descriptions are omitted as necessary for the sake of clarity of explanation. In addition, the features of each example embodiment can be combined as long as there is no technical contradiction.

First Example Embodiment

FIG. 1 is a block diagram showing an example of a configuration of an information processing device 1 according to a first example embodiment. The information processing device 1 is a device that supports an examination by a user (for example, a doctor) using an endoscope, and performs display processing related to detection of a lesion. As shown in FIG. 1, the information processing device 1 includes a first acquisition unit 2, a second acquisition unit 3, and a display control unit 4.

The first acquisition unit 2 acquires a capturing time of a lesion image that the user has instructed to save, from a series of images captured by an endoscope during examination with the endoscope. The capturing time may be an absolute time such as a system time at the time of capturing, or may be a relative time with reference to a start time of capturing. For example, the first acquisition unit 2 may acquire the above-described capturing time based on log data of the endoscope system, or may acquire the capturing time by analyzing a moving image output from the endoscope system to specify the above-described capturing time. The lesion image refers to an image including a lesion site, that is, an image in which the lesion site is detected. Here, the lesion refers to an abnormality in a biological tissue caused by a disease, the abnormality including, for example, a polyp or a tumor, but being not limited thereto. The user instructs the endoscope system to save an image showing the lesion site visually recognized by the user during the examination with the endoscope. Therefore, the lesion image instructed to be saved by the user can be regarded as a lesion image showing the lesion site visually recognized by the user.

The second acquisition unit 3 acquires a capturing time of a lesion image detected by detection processing for a series of images captured by the endoscope in the midst of examination. The detection processing is processing of performing any image recognition processing to detect a lesion site depicted in an image. Therefore, the second acquisition unit 3 acquires a capturing time of the image (lesion image) in which the lesion site is detected by the detection processing, in other words, a capturing time of the lesion image in which the lesion site detected by the detection processing is depicted.

The display control unit 4 controls a display of information on a display device. Specifically, the display control unit 4 causes the display device to display a first capturing time which is the capturing time acquired by the first acquisition unit 2 and a second capturing time which is the capturing time acquired by the second acquisition unit 3 on a time axis in a plotting manner.

According to the present example embodiment, the capturing time of the lesion image that the user has instructed to save during the examination with the endoscope, that is, the capturing time of the lesion image for the lesion detected by the user and the capturing time of the lesion image for the lesion detected by the detection processing are plotted on the time axis. Therefore, both of the capturing times can be compared with each other on the time axis. In other words, according to the present example embodiment, it is possible to show the detection by the user and the detection by the detection processing in comparison with each other at what time during the examination the lesion to be captured is detected. Therefore, it is possible to easily recognize the discrepancy between the detection result of the detection processing for the image captured by the endoscope and the detection result by the user. For example, when a lesion image is obtained during one detection and no lesion image is obtained during the other detection at a certain time zone during the examination, it is possible to easily grasp that there is a discrepancy in detection results during the detection in such a time zone.

The information processing device 1 includes a processor and a memory as components which are not shown. The processor reads a computer program, in which the above-described processing of the information processing device 1 is implemented, from the memory, and executes the computer program. Thus, the processor realizes functions of the first acquisition unit 2, the second acquisition unit 3, and the display control unit 4.

Alternatively, each of the first acquisition unit 2, the second acquisition unit 3, and the display control unit 4 may be realized by dedicated hardware. Further, a part or all of components of each device may be realized by a general-purpose or dedicated circuitry, a processor, or a combination thereof. The components may be configured by a single chip, or may be configured by a plurality of chips connected to each other via a bus. A part or all of components of each device may be realized by a combination of the circuitry and the program described above. In addition, as a processor, a CPU (Central Processing Unit) or a GPU (Graphics Processing Unit) can be used.

Further, when a part or all of the components of the information processing device 1 are realized by a plurality of information processing devices and circuits, the plurality of information processing devices and the circuits may be arranged in a centralized manner, or may be arranged in a distributed manner. For example, the information processing devices and the circuits may be realized as a form of being connected to each other via a communication network such as a client-and-server system or a cloud computing system. Further, the function of the information processing device 1 may be provided in SaaS (Software as a Service) format.

Example embodiments will be described below in which the first example embodiment is made more specific.

Second Example Embodiment

Figure 2:
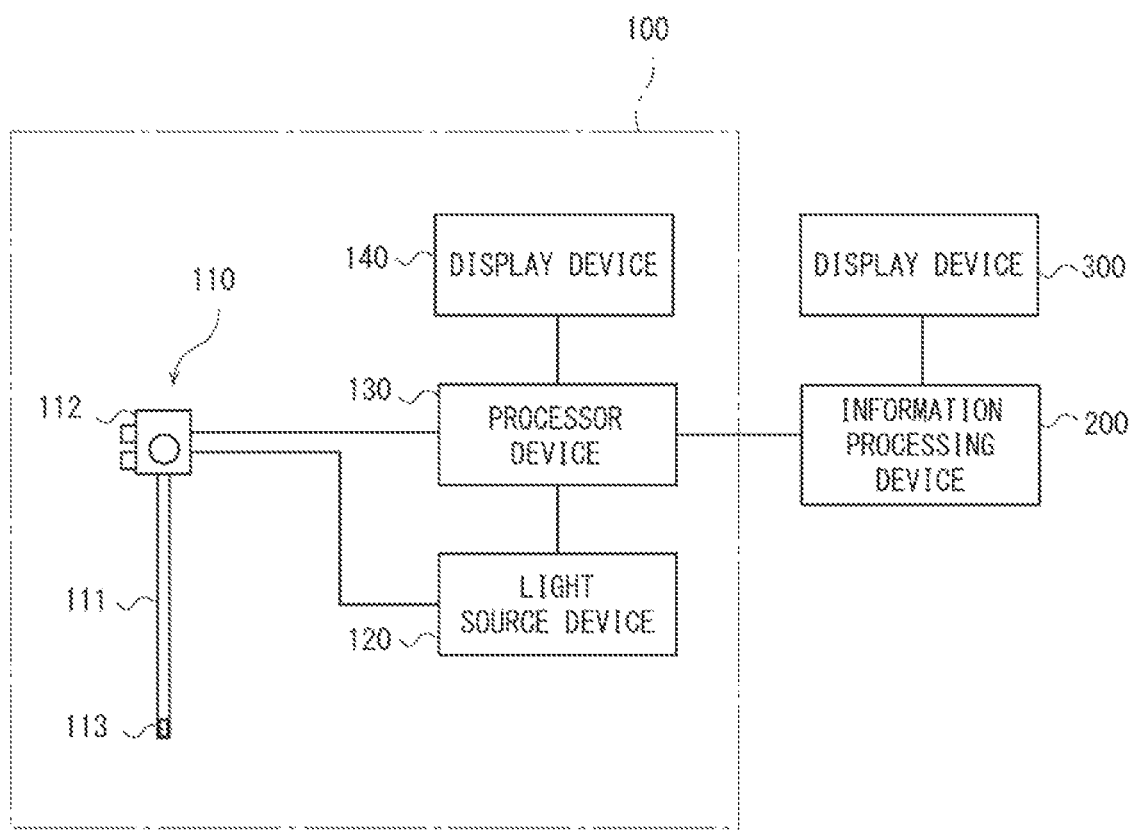
FIG. 2 is a block diagram showing a configuration of an examination support system according to a second example embodiment.

FIG. 2 is a block diagram showing a configuration of an examination support system 10 according to a second example embodiment. The examination support system 10 includes an endoscope system 100, an information processing device 200, and a display device 300. The endoscope system 100 is used to examine body cavities of a subject to be examined. For example, the endoscope system 100 is used to examine a large intestine, but may be used to examine other digestive tracts.

The endoscope system 100 includes an endoscope 110, a light source device 120, a processor device 130, and a display device 140. The endoscope 110 is optically connected to the light source device 120, and further electrically connected to the processor device 130.

The endoscope 110 includes an insertion portion 111 (an insertion unit 111) to be inserted into the body of a person who is a subject to be examined and an operation portion 112 (an operation unit 112) configured to operate a direction of a distal end of the insertion portion 111. An image capturing portion 113 (an image capturing unit 113) is provided at the endoscope 110 to capture an in-vivo image of the body. The image capturing portion 113 includes, for example, various lenses, an image capturing sensor, and a signal processing circuit. As the image capturing sensor, a sensor such as a CCD (Charge Coupled Device) or a CMOS (Complementary Metal-Oxide Semiconductor) is used. The various lenses and the image capturing sensor are disposed at the distal end of the insertion portion 111, for example, and the other signal processing circuits are disposed at the operation portion 112, for example. The image capturing portion 113 outputs an image signal of the captured image to the processor device 130 under the control of the processor device 130.

A light guide is provided inside the insertion portion 111 to propagate illumination light from the light source device 120 to the distal end of the insertion portion 111, and the inside of the body can be illuminated by the illumination light. Further, the insertion portion 111 is provided with a treatment-instrument insertion passage through which a treatment instrument such as electrocautery is guided from the operation portion 112 to the distal end of the insertion portion 111. Therefore, the user (doctor) can excise the lesion site with the treatment instrument while looking at the image captured by the endoscope 110. In addition, the insertion portion 111 is provided with a nozzle for ejecting air or water from the distal end of the insertion portion 111.

The light source device 120 is a device that supplies the illumination light to the above-described light guide provided in the endoscope 110 under the control of the processor device 130. The illumination light output from the light source device 120 is emitted from the distal end of the endoscope 110 by passing through the light guide. Thus, an in-vivo observation site is irradiated with the illumination light.

The processor device 130 is electrically connected to the endoscope 110, the light source device 120, the display device 140, and the information processing device 200. Further, the processor device 130 is connected to an input device that receives an input of an instruction from the user. Particularly, in the present embodiment, the input device receives, as an input, an instruction to save the image captured by the endoscope 110 during the examination with the endoscope 110. Such an input device may be provided as a function of the operation portion 112, or when the display device 140 is configured by a touch panel, the touch panel may function as such an input device. An input device such as a keyboard or a mouse provided independently of the above-described configuration may be used.

Figure 3:
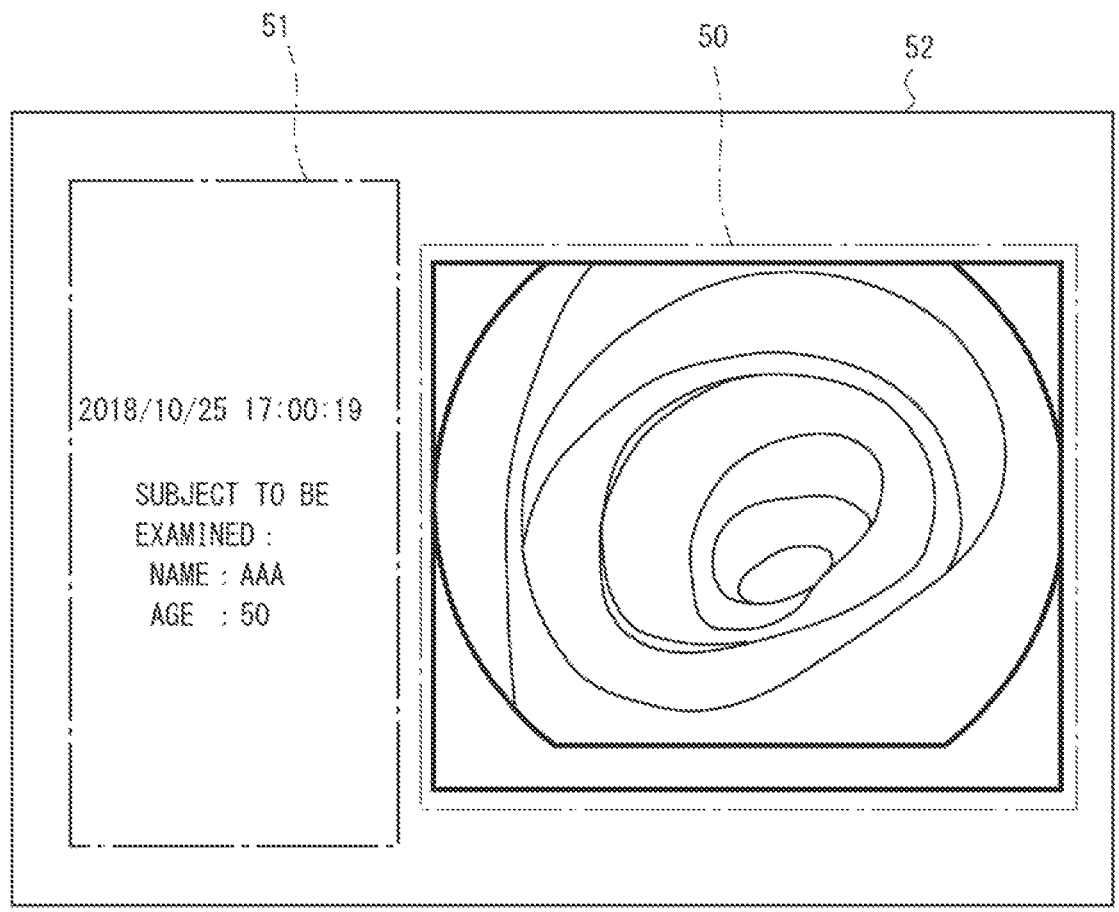
FIG. 3 is a schematic diagram showing an example of a display screen generated by a processor device.

The processor device 130 comprehensively controls an operation of the endoscope system 100. Particularly, the processor device 130 performs predetermined image processing on the image signal received from the endoscope 110, and generates a captured image to be displayed on the display device 140. Further, as shown in FIG. 3, the processor device 130 generates a display image 52 in which a captured image is arranged in a captured image area 50 and characters or images of various reference information such as information on the subject to be examined are arranged in a non-captured image area 51. The display image 52 is an image displayed on the entire screen of the display device 140. The processor device 130 controls the display device 140 to display the display image 52. In addition, the processor device 130 outputs the display image 52 to the information processing device 200. The processor device 130 may output the captured image to the information processing device 200. In this way, the processor device 130 outputs the display image 52 or the captured image to the information processing device 200, and thus sequentially outputs the current image captured by the endoscope 110 to the information processing device 200. In other words, the processor device 130 outputs the moving image captured by the endoscope 110, that is, a series of images of the body cavity captured continuously in time to the information processing device 200 in real time. In the present embodiment, the processor device 130 outputs the image to the information processing device 200 in real time in order to detect the lesion site in real time during the examination in the information processing device 200 to be described below, but does not necessarily output the image in real time. In other words, when the lesion site is not necessary to be detected in real time by the information processing device 200, the processor device 130 does not have to output the captured image in real time. For example, the captured image that is captured during the examination may be output to the information processing device 200 at any time after the examination is completed and a series of capturing is completed. In this way, the processor device 130 functions as an image output device that outputs the image captured by the endoscope 110.

Further, upon receiving, as an input, the instruction to save the captured image during the capturing with the endoscope 110, the processor device 130 saves image data of the captured image at the timing of receiving the input in a storage device such as a memory. The user regards the captured image showing the lesion site as a target to be saved, for example. Therefore, when the user inputs the instruction to save the lesion image during the capturing with the endoscope 110, the processor device 130 saves the image data of captured image at the timing when the input is received. In other words, the processor device 130 saves the lesion image that user has instructed to save out of the series of images captured by the endoscope 110 during the examination with the endoscope 110.

In the present embodiment, when the user instructs to save the lesion image during the examination with the endoscope 110, the processor device 130 outputs an image with a predetermined feature until a certain time elapses from the time of the instruction. Specifically, for example, the processor device 130 outputs the captured image to be saved until a certain time elapses from the time of the instruction. In other words, during this period, the processor device 130 continuously outputs the same image. In other words, the processor device 130 outputs an image having a feature of being the same as the previous image during this period. Thus, a frozen image is output to the display device 140 and the information processing device 200, as an image of a series of images during this period. By such processing, the display device 140 displays the image having a predetermined feature until a certain time elapses from the time of the instruction. Therefore, the user can grasp that the captured image has been saved by the processor device 130 in response to his/her instruction.

The predetermined feature is not limited to the above-described feature, and may be another feature. For example, until a certain time elapses from the time of the instruction, the display image 52 arranged with not only the captured image but also a thumbnail image of the image to be saved may be output to the display device 140 and the information processing device 200. In this case, during this period, the processor device 130 outputs an image having a feature that the thumbnail image is arranged in a predetermined area.

The processor device 130 includes, for example, a memory and a processor such as a CPU and a GPU, and the processor reads software (computer program) including one or more commands from the memory and executes the software to realize the processing of the processor device 130.

The display device 140 displays the display image 52 generated by the processor device 130. Specifically, the display device 140 is a flat panel display such as a liquid crystal display, a plasma display, or an organic EL (Electro-Luminescence) display.

Next, the information processing device 200 and the display device 300 will be described.

The display device 300 is electrically connected to the information processing device 200, and is a device that displays an image under the control of the information processing device 200. Specifically, the display device 300 is a flat panel display such as a liquid crystal display, a plasma display, or an organic EL display. In the present embodiment, the display device 300 is configured as a touch panel, and also functions as an input device that receives the input from the user.

The information processing device 200 corresponds to the information processing device 1 shown in FIG. 1, and is a device that supports the examination by the user (for example, a doctor). Details of the information processing device 200 will be described below.

Figure 4:
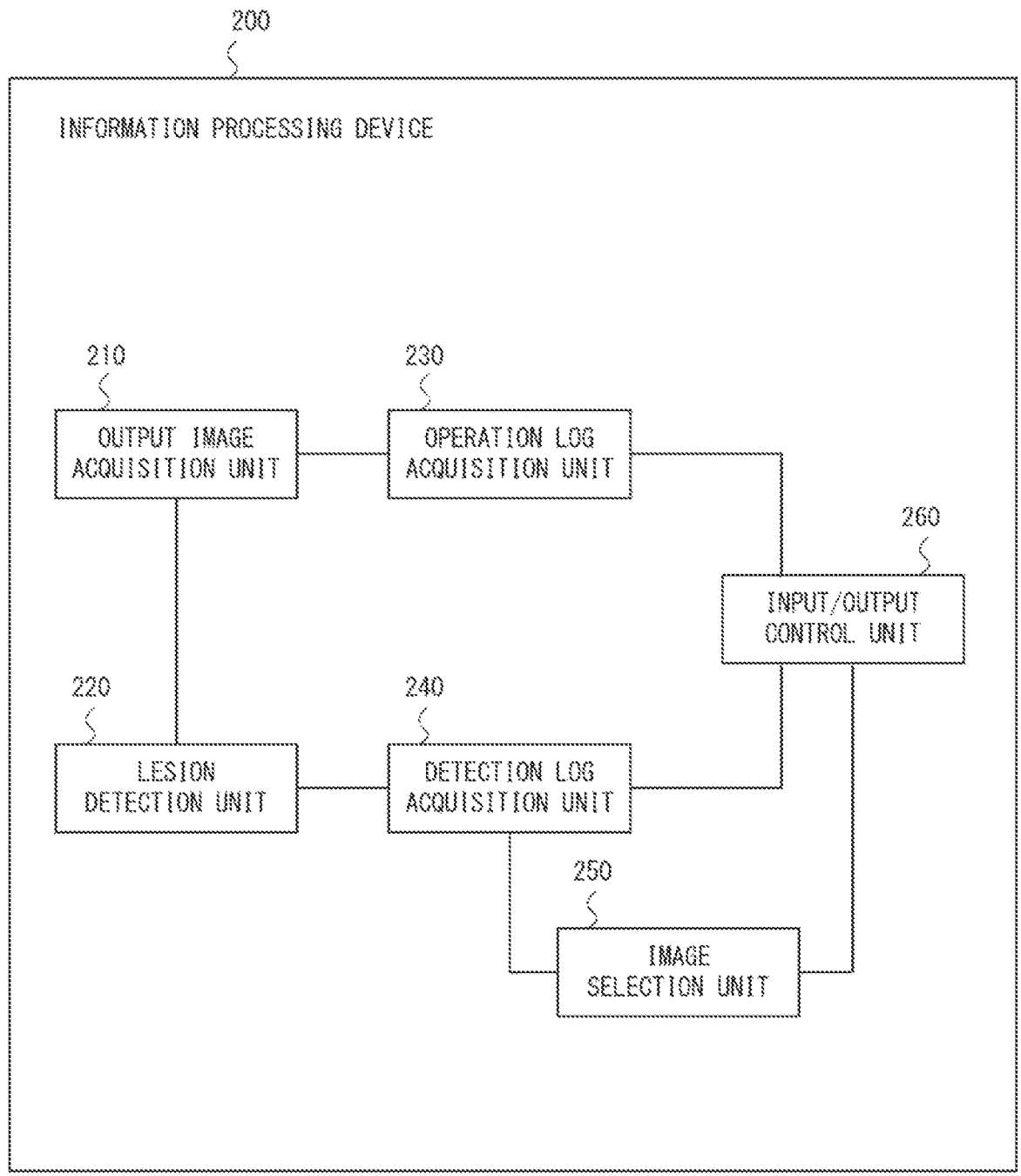
FIG. 4 is a block diagram showing an example of a functional configuration of an information processing device according to the second example embodiment.

FIG. 4 is a block diagram showing an example of a functional configuration of the information processing device 200. As shown in FIG. 4, the information processing device 200 includes an output image acquisition unit 210, a lesion detection unit 220, an operation log acquisition unit 230, a detection log acquisition unit 240, an image selection unit 250, and an input/output control unit 260.

The output image acquisition unit 210 acquires an image group (each frame image (still image) constituting the captured moving image) output by the processor device 130. In other words, the output image acquisition unit 210 acquires a series of images captured by the endoscope 110 during the examination with the endoscope 110. More specifically, the output image acquisition unit 210 acquires, from the processor device 130, a series of images of the body cavity captured continuously in time. In the present embodiment, the output image acquisition unit 210 sequentially acquires current images captured by the endoscope 110 in real time, but does not necessarily acquire the images in real time. When the display image 52 is output from the processor device 130, the output image acquisition unit 210 performs processing of cutting out the captured image arranged in the captured image area 50 from the display image 52, thereby obtaining the captured image used for the processing of the lesion detection unit 220.

The lesion detection unit 220 sequentially performs detection processing of a lesion site on the image acquired by the output image acquisition unit 210. In other words, the lesion detection unit 220 sequentially performs detection processing of a lesion site on each frame image constituting the captured moving image. In the present embodiment, the lesion detection unit 220 performs the detection processing of the lesion site in real time. For example, the lesion detection unit 220 preferably performs the detection processing at a processing speed faster than a frame rate of the captured moving image. The lesion detection unit 220 detects the lesion site from the image by performing known image recognition processing. In such detection processing, a position of the lesion site in the image is also detected. For example, the lesion detection unit 220 performs the detection processing of the lesion site by inputting the image, which is acquired by the output image acquisition unit 210, to a model learned in advance by a machine learning algorithm. Such a model is, for example, a model learned by deep learning such as CNN (Convolution Neural Network), but may be a model learned by using another machine learning algorithm. For example, based on whether an index value (accuracy) indicating the probability that the lesion site is depicted in an image output from the model described above exceeds a predetermined threshold value, the lesion detection unit 220 determines whether the lesion site is depicted in the image.

When detecting the lesion site, the lesion detection unit 220 stores the lesion image, position information in the image of the detected lesion site, the index value described above, and information indicating the capturing time of the lesion image (hereinafter, referred to as capturing time information) in a storage device such as a memory 291, which will be described below, as a log. Here, the capturing time information may be any information that can specify the time of the capturing. For example, the capturing time information is a system time at the time of the capturing. As described above, the captured image is acquired by the output image acquisition unit 210 in real time, and the lesion detection processing is performed in real time. Therefore, the lesion detection unit 220 may use the time when the information processing device 200 acquires the image, as capturing time information of the image, or may use the time when the lesion detection unit 220 performs the lesion detection processing, as capturing time information of the image. In addition, the capturing time information may be incidental information incidental to the image data by the processor device 130. As described above, the capturing time information may be any information that can specify the time when the capturing is performed, and thus the frame number of the moving image may be used instead of the system time.

The operation log acquisition unit 230 corresponds to the first acquisition unit 2 shown in FIG. 1. The operation log acquisition unit 230 acquires a capturing time of a lesion image that the user has instructed to save, from a series of images captured by an endoscope 110 in the midst of examination with the endoscope 110. Further, the operation log acquisition unit 230 acquires the lesion image instructed to be saved by the user. In the following description, the acquired capturing time and the lesion image may be referred to as a log.

In the present embodiment, the operation log acquisition unit 230 acquires the capturing time of the lesion image instructed to be saved by the user and the lesion image by analyzing a series of frame image (that is, moving images) output by the processor device 130. Specifically, the operation log acquisition unit 230 determines, based on the presence or absence of a predetermined feature in the acquired captured image, whether the capturing time of the captured image is the time when the instruction to save is generated. When the predetermined feature exists in the acquired captured image, the operation log acquisition unit 230 determines that the instruction to save is input at the capturing time of the captured image. Then, the operation log acquisition unit 230 acquires the captured image as a lesion image instructed to be saved by the user, and acquires the capturing time of the captured image as the capturing time of the lesion image instructed to be saved by the user. The operation log acquisition unit 230 may acquire a time point around a predetermined time from the capturing time of the captured image, as the capturing time of the lesion image instructed to be saved by the user. In this way, the operation log acquisition unit 230 determines, based on the presence or absence of the predetermined feature in the image acquired by the output image acquisition unit 210, the time point at which the instruction to save is generated, and thus acquires the capturing time of the lesion image instructed to be saved by the user and the lesion image.

As described above, in the present embodiment, when the user instructs to save the lesion image during the examination with the endoscope 110, the processor device 130 outputs a frozen image as a captured image until a certain time elapses from the instruction time. In the present embodiment, accordingly, the operation log acquisition unit 230 determines the time point at which the instruction to save is generated, based on whether the image to be determined is the same as the image of a previous frame, and thus acquires the capturing time of the lesion image instructed to be saved by the user and the lesion image. When the processor device 130 outputs an image having another feature as a predetermined feature until a certain time elapses from the instruction time, the operation log acquisition unit 230 may determine the presence or absence of such another feature. For example, the operation log acquisition unit 230 may determine whether a thumbnail image is arranged in the image acquired by the output image acquisition unit 210.

According to such processing of the operation log acquisition unit 230, the lesion image instructed to be saved by the user and the information indicating the capturing time of the lesion image (capturing time information) are acquired without acquisition of the log data from the processor device 130. The lesion image acquired by the operation log acquisition unit 230 is an image presumed to be the lesion image instructed to be saved by the user as described above. In other words, the operation log acquisition unit 230 searches for an image presumed to be the lesion image instructed to be saved by the user, from the image group acquired by the output image acquisition unit 210, and acquires the image. Further, similarly to the capturing time information stored by the lesion detection unit 220, the capturing time information acquired by the operation log acquisition unit 230 may be, for example, the system time at the time point when the capturing is performed. In this case, the operation log acquisition unit 230 may use the time when the output image acquisition unit 210 acquires the image in real time, as the capturing time information of the image, or may use the time when the lesion detection unit 220 performs the lesion detection processing in real time, as capturing time information of the image. In addition, the capturing time information acquired by the operation log acquisition unit 230 may be incidental information incidental to the image data by the processor device 130. As the capturing time information, the frame number of the moving image may be used instead of the system time.

Although the operation log acquisition unit 230 acquires, from the processing described above, the information regarding the operation of the instruction to save during the examination, the log data may be acquired from the processor device 130. In other words, the operation log acquisition unit 230 may acquire the capturing time of the lesion image instructed to be saved by the user and the lesion image which are output as log data by the processor device 130. In this case, the operation log acquisition unit 230 may not perform the above-described determination processing of determining, based on the presence or absence of the predetermined feature, the time point at which the instruction to save is generated.

The detection log acquisition unit 240 corresponds to the second acquisition unit 3 shown in FIG. 1. The detection log acquisition unit 240 acquires a capturing time of a lesion image detected by detection processing on a series of images captured by an endoscope 110 in the midst of examination with the endoscope 110. Further, the detection log acquisition unit 240 acquires the lesion image detected by the detection processing. In the present embodiment, the detection log acquisition unit 240 acquires the lesion image and the capturing time information of the lesion image which are stored in the storage device as log data by the lesion detection unit 220, from the storage device.

The image selection unit 250 specifies a plurality of lesion images in which the same lesion site is detected by the detection processing of the lesion detection unit 220, and selects one image (hereinafter, referred to as a representative image) from the plurality of specified lesion images. In the present embodiment, the image selection unit 250 specifies a plurality of lesion images, in which the same lesion site is detected, from the lesion image group acquired by the detection log acquisition unit 240, and selects a representative image from the plurality of lesion images. For example, the image selection unit 250 compares the lesion images with each other to specify a plurality of lesion images in which the same lesion site is detected. More specifically, the image selection unit 250 performs object track processing using feature points of the lesion site on continuous captured images (frame image) constituting the captured moving image among the lesion images acquired by the detection log acquisition unit 240. Thus, the image selection unit 250 specifies a plurality of lesion images in which the same lesion site is detected. By such processing, a plurality of images are specified in which the same lesion site is depicted, the plurality of images being obtained when the same lesion site is continuously captured in time. Then, the image selection unit 250 selects a representative image from the plurality of lesion images in which the same lesion site is detected. The image selection unit 250 selects, for example, a lesion image having the highest detection accuracy in the detection processing from these plurality of lesion images. When there are a plurality of lesion images having the highest detection accuracy in the detection processing, the image selection unit 250 may select, from these lesion images, an image in which the lesion site can be easily seen. For example, the image selection unit 250 may select an image of which position in the image of the lesion site is closest to the center, as the image in which the lesion site is easily seen, or may select an image in which the contrast between the lesion site and the non-lesion site is maximum. The image selection unit 250 may specify a plurality of lesion images, in which the same lesion site is detected, by processing of calculating the similarity of images instead of the object track processing. In this case, it is possible to specify a plurality of images in which the same lesion site is depicted even when the same lesion site is not continuously captured in time.

The image selection unit 250 may select a plurality of images as representative images. Particularly, the image selection unit 250 may select two or more images having different capturing conditions from the plurality of lesion images in which the same lesion site is detected. For example, the image selection unit 250 may select two or more images having different capturing angles, or may select two or more images having different capturing distances. Thus, various images will be displayed as representative images.

The input/output control unit 260 controls input and output of information in the information processing device 200. The information processing device 200 is connected to an input device that receives an input of an instruction from the user, and the input/output control unit 260 receives the input from the input device. Particularly, in the present embodiment, the input device receives an input from a user who sees the display of the display device 300. In the present embodiment, the display device 300 is configured as a touch panel, and the display device 300 also functions as an input device. An input device such as a keyboard or a mouse provided independently of the display device 300 may be used.

In addition, the input/output control unit 260 controls the display of the display device 300. The input/output control unit 260 corresponds to the display control unit 4 shown in FIG. 1. Therefore, in particularly, the input/output control unit 260 controls the display device 300 to display the capturing time acquired by the operation log acquisition unit 230 and the capturing time acquired by the detection log acquisition unit 240 which are plotted on a time axis. In other words, the input/output control unit 260 controls to display the capturing time of the lesion image saved by the instruction from the user and the capturing time of the lesion image in which the lesion is detected by the lesion detection unit 220 which are plotted on a time axis. In the present embodiment, the input/output control unit 260 further displays the lesion image in association with the capturing time. In other words, the input/output control unit 260 displays the lesion image saved by the instruction from the user in association with the capturing time of the lesion image. Similarly, the input/output control unit 260 displays the lesion image in which the lesion is detected by the lesion detection unit 220 in association with the capturing time of the lesion image. More specifically, as shown in FIG. 5 and the like to be described below, the input/output control unit 260 displays a thumbnail image of the lesion image.

Figure 5:
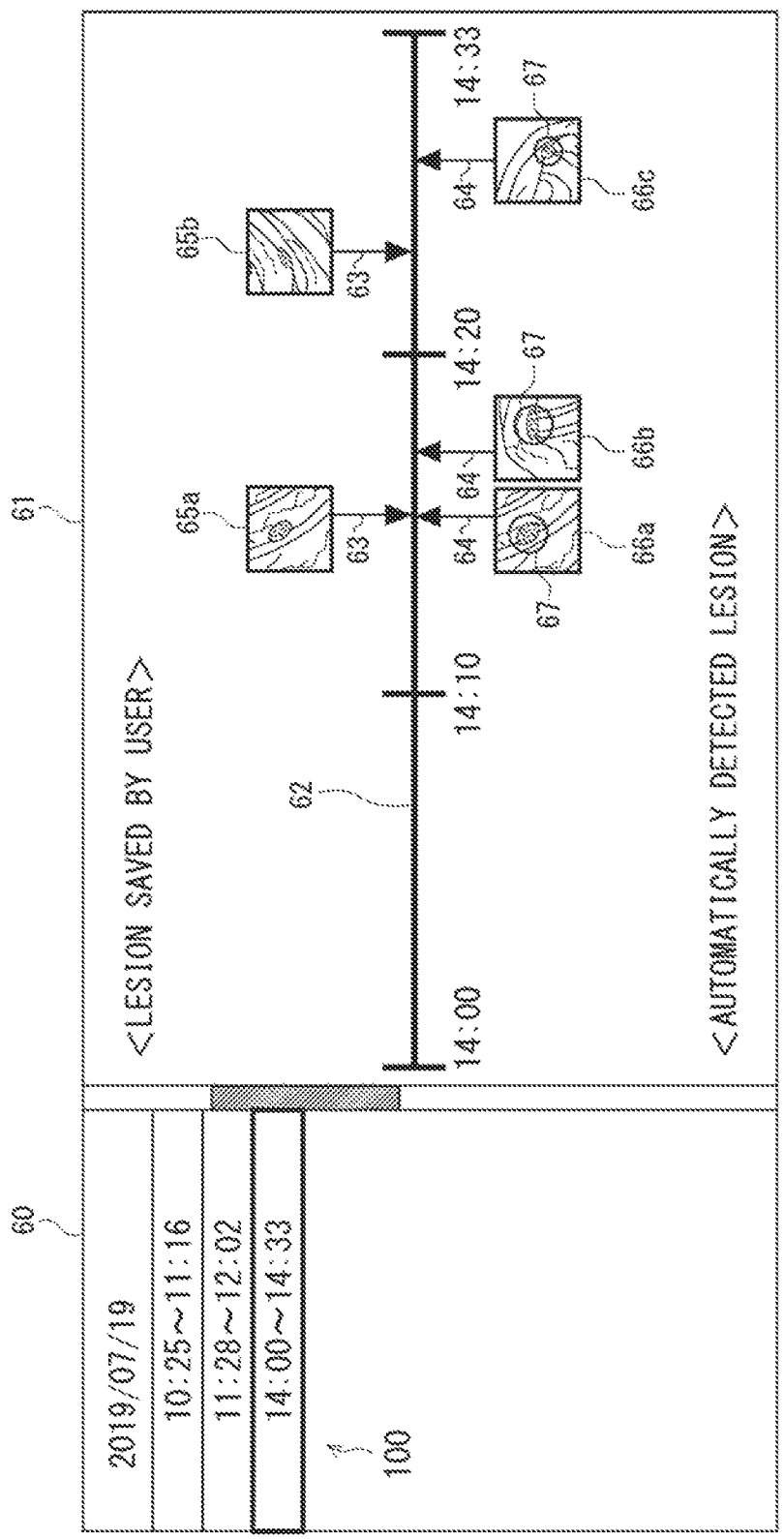
FIG. 5 is a schematic diagram showing a display example based on control of an input/output control unit.

FIG. 5 is a schematic diagram showing a display example of the display device 300 based on the control of the input/output control unit 260. Display control of the input/output control unit 260 of the present embodiment will be described with reference to FIG. 5.

The input/output control unit 260 displays a list of examination capable of displaying logs in a log list area 60 on a screen of the display device 300. In the example shown in FIG. 5, three kinds of examination performed on Jul. 19, 2019 are listed. In the example shown in FIG. 5, as each item in the list, a time is displayed during which the examination is performed. In other words, a start time of the examination and an end time of the examination are displayed. The input/output control unit 260 performs the display as shown in FIG. 5 by setting a capturing time of the first image of the series of images acquired by the output image acquisition unit 210 as a start time of examination and specifying a capturing time of the last image of the series of images as an end time of examination, for example.

The input/output control unit 260 displays, in a log display area 61 on the screen of the display device 300, the information acquired by the operation log acquisition unit 230 and the detection log acquisition unit 240, when the input is received from the user to select one of the items from the list displayed in the log list area 60. In the example shown in FIG. 5, the log for the examination performed at the examination time from 14:00 to 14:33 is displayed.

The input/output control unit 260 displays, in the log display area 61, a time axis 62, a mark 63 indicating the capturing time acquired by the operation log acquisition unit 230 on the time axis 62, and a mark 64 indicating the capturing time acquired by the detection log acquisition unit 240 on the time axis 62. Further, the input/output control unit 260 displays a lesion image corresponding to the capturing time acquired by the operation log acquisition unit 230 and a lesion image corresponding to the capturing time acquired by the detection log acquisition unit 240. In more detail, a thumbnail image of the lesion image is displayed. In the example shown in FIG. 5, lesion images 65a and 65b are displayed as lesion images corresponding to the capturing time acquired by the operation log acquisition unit 230, and lesion images 66a, 66b, and 66c are displayed as lesion images corresponding to the capturing time acquired by the detection log acquisition unit 240. In the example shown in FIG. 5, the marks 63 and 64 are arrows as an example. In the example shown in FIG. 5, a display related to the information acquired by the operation log acquisition unit 230 is performed on an upper side of the time axis 62. In other words, a display related to the lesion image saved by the user is performed on the upper side of the time axis 62. The input/output control unit 260 displays the lesion image acquired by the operation log acquisition unit 230 as the lesion image detected by the user (for example, a doctor). On the other hand, a display related to the information acquired by the detection log acquisition unit 240 is performed on a lower side of the time axis 62. In other words, a display related to the lesion automatically detected by the detection processing performed by the lesion detection unit 220 is performed on the lower side of the time axis 62. The example shown in FIG. 5 is merely an example, and it goes without saying that the display content on the upper side and the display content on the lower side of the time axis 62 may be reversed. In the example shown in FIG. 5, the time axis 62 extends in a horizontal direction of the screen, but the time axis 62 may extend in another direction.

In the example shown in FIG. 5, the input/output control unit 260 displays scales of the time axis 62, but the scales of the time axis 62 may not be displayed. In the example shown in FIG. 5, the start time of the examination is displayed as a scale at a beginning end of the time axis 62, and the end time of the examination is displayed as a scale at a terminated end of the time axis 62, but the scale is not necessarily associated with the examination time. For example, a value of the scale at the beginning end of the time axis 62 may be set to 0, and a value of the scale at the terminated end of the time axis 62 may be a value equivalent to a time length of the captured image.

The input/output control unit 260 may display the position in the image of the lesion site detected by the lesion detection unit 220. In the example shown in FIG. 5, specifically, the input/output control unit 260 displays a frame 67 surrounding the lesion site.

Figure 6:
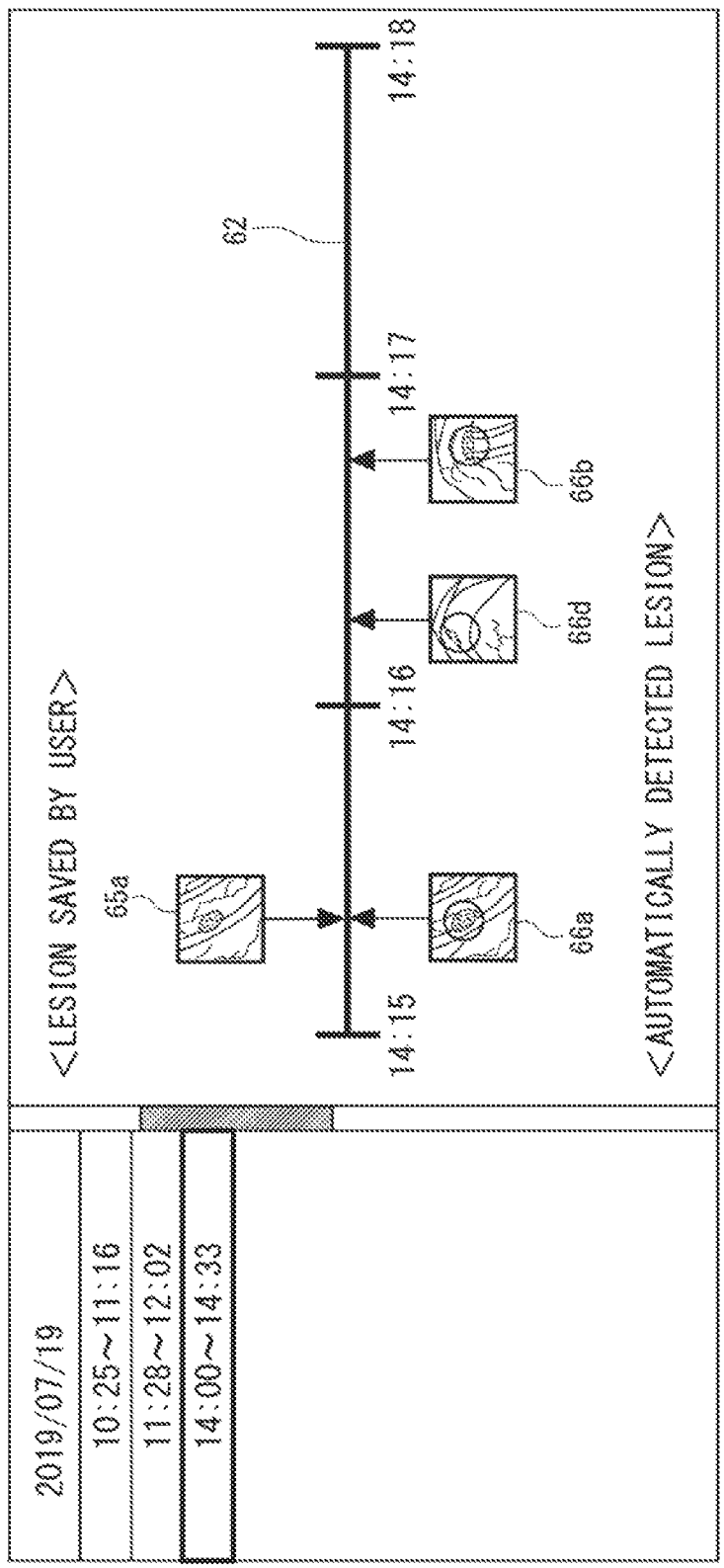
FIG. 6 shows a display example when a scale of a time axis shown in FIG. 5 is enlarged.
Figure 7:
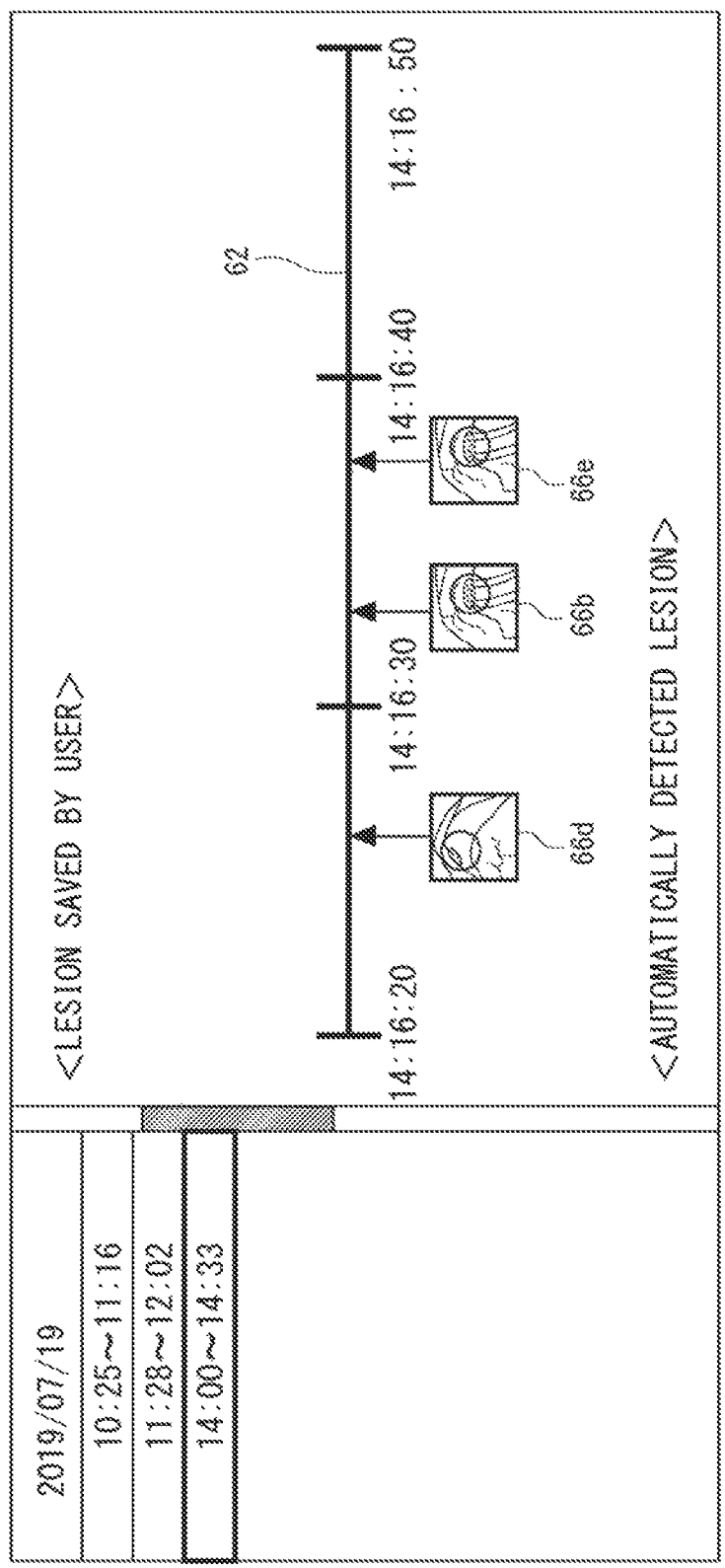
FIG. 7 shows a display example when a scale of a time axis shown in FIG. 6 is enlarged.

Further, as shown in FIGS. 5 to 7, the input/output control unit 260 displays, based on the instruction input from the user, the scale of the time axis 62 in an enlarged or reduced manner. The input/output control unit 260 may change the scale of the time axis 62 when an operation of touching (tapping) or clicking the time axis 62 is performed as such an instruction, for example. Thereby, it is possible to improve the convenience in browsing the log.

FIG. 6 shows a display example when the scale of the time axis 62 shown in FIG. 5 is enlarged. In the example shown in FIG. 6, the scale of the time axis 62 is enlarged as compared with the example shown in FIG. 5, and a log of a time zone from 14:15 to 14:18 is displayed as an examination time. In addition, FIG. 7 shows a display example when the scale of the time axis 62 shown in FIG. 6 is enlarged. In the example shown in FIG. 7, the scale of the time axis 62 is enlarged as compared with the example shown in FIG. 6, and a log of a time zone from 14:16:20 to 14:16:50 is displayed as an examination time.

The input/output control unit 260 may change a log actually displayed among the logs of the time zone to be displayed according to the scale of the time axis 62. As shown in FIG. 5, in the display where the scale is reduced, there is a concern that the display may be complicated when all the logs belonging to the time zone to be displayed (specifically, from 14:00 to 14:33 in FIG. 5) are displayed. Therefore, for example, when the time axis 62 is displayed with a scale smaller than a predetermined scale, the input/output control unit 260 may display only some of the logs of the time zone to the displayed. In other words, the input/output control unit 260 may display only some of the capturing times and the captured image corresponding to the capturing time. In such a case, as for the capturing time, all the capturing time in the time zone to be displayed may be displayed, and only the display of the captured image may be limited to some of the captured images. During the selection of some of the captured images, the input/output control unit 260 may select it according to an arbitrary selection criterion. For example, the input/output control unit 260 may select the image based on the magnitude of the accuracy of detection in the detection processing.

The display of some of the logs described above will be described in detail with reference to the drawings. In the example shown in FIG. 6, lesion images 66a, 66d, and 66b are displayed as logs of the detection processing of the lesion detection unit 220 in the time zone from 14:15 to 14:18. On the other hand, in the example shown in FIG. 5, focusing on the same time zone as in FIG. 6, only the lesion images 66a and 66b are displayed as the logs of the detection processing of the lesion detection unit 220. Similarly, in the example shown in FIG. 7, lesion images 66d, 66b, and 66e are displayed as logs of the detection processing of the lesion detection unit 220 in the time zone from 14:16:20 to 14:16:50. On the other hand, in the example shown in FIG. 6, focusing on the same time zone as in FIG. 7, only the lesion images 66d and 66b are displayed as the logs of the detection processing of the lesion detection unit 220.

Further, the input/output control unit 260 may display only the lesion image selected as a representative image by the above-described image selection unit 250, from the plurality of lesion images in which the same lesion site is detected. In other words, the lesion image may not be displayed which is not selected as the representative image from the plurality of lesion images in which the same lesion site is detected. At this time, the input/output control unit 260 may display the capturing time of the lesion image selected as the representative image, and may not display the capturing time of the lesion image not selected as the representative image from the plurality of lesion images in which the same lesion site is detected. Thereby, the repeated lesions are not displayed, and visibility is improved. In the present embodiment, when the time axis 62 is displayed with a scale smaller than a predetermined scale, the input/output control unit 260 displays only the lesion image selected as the representative image from the plurality of lesion images in which the same lesion site is detected. A specific example thereof will be described with reference to the drawings. In the example shown in FIG. 7, the lesion image 66b and the lesion image 66e are displayed in which the same lesion site is captured, whereas in the example shown in FIG. 6, only the lesion image 66b is displayed which is selected as the representative image from these captured images.

Figure 8:
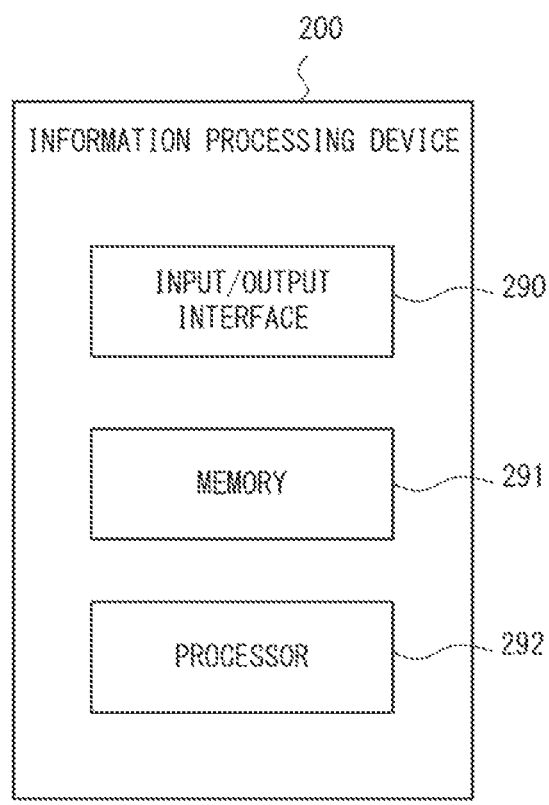
FIG. 8 is a schematic diagram showing an example of a hardware configuration of the information processing device according to the first example embodiment.

An example of a hardware configuration of the information processing device 200 will be described below. FIG. 8 is a schematic diagram showing an example of a hardware configuration of the information processing device 200. As shown in FIG. 8, the information processing device 200 includes an input/output interface 290, a memory 291, and a processor 292.

The input/output interface 290 is an input/output circuit configured to communicate with any other devices, for example, the processor device 130 and the display device 300.

The memory 291 is configured by a combination of a volatile memory and a non-volatile memory, for example. The memory 291 is used to store software (computer program) and data used for various processing of the information processing device 200, the software including one or more commands executed by the processor 292.

The processor 292 reads and executes the software (computer program) from the memory 291 to perform the processing of each component shown in FIG. 4. Specifically, the processor 292 performs the processing of the output image acquisition unit 210, the lesion detection unit 220, the operation log acquisition unit 230, the detection log acquisition unit 240, the image selection unit 250, and the input/output control unit 260.

The processor 292 may be, for example, a CPU or a GPU. The processor 292 may include a plurality of processors.

As described above, the information processing device 200 has a function as a computer.

The above-described programs may be stored and supplied to a computer using various types of non-transitory computer readable media. The non-transitory computer readable media include various types of tangible storage media. Examples of the non-transitory computer readable media include a magnetic recording medium (for example, a flexible disk, a magnetic tape, and a hard disk drive), a magneto-optic recording medium (for example, a magneto-optic disk), a CD-ROM (Read Only Memory), a CD-R, a CD-R/W, and a semiconductor memory (for example, a mask ROM, a PROM (Programmable ROM), an EPROM (Erasable PROM), a flash ROM, and a RAM (Random Access Memory)). These programs may be supplied to computers using various types of transitory computer readable media. Examples of the transitory computer readable media include an electrical signal, an optical signal, and an electromagnetic wave. The transitory computer readable media can supply programs to a computer through a wired communication line, for example, electric wires and optical fibers, or a wireless communication line.

Figure 9:
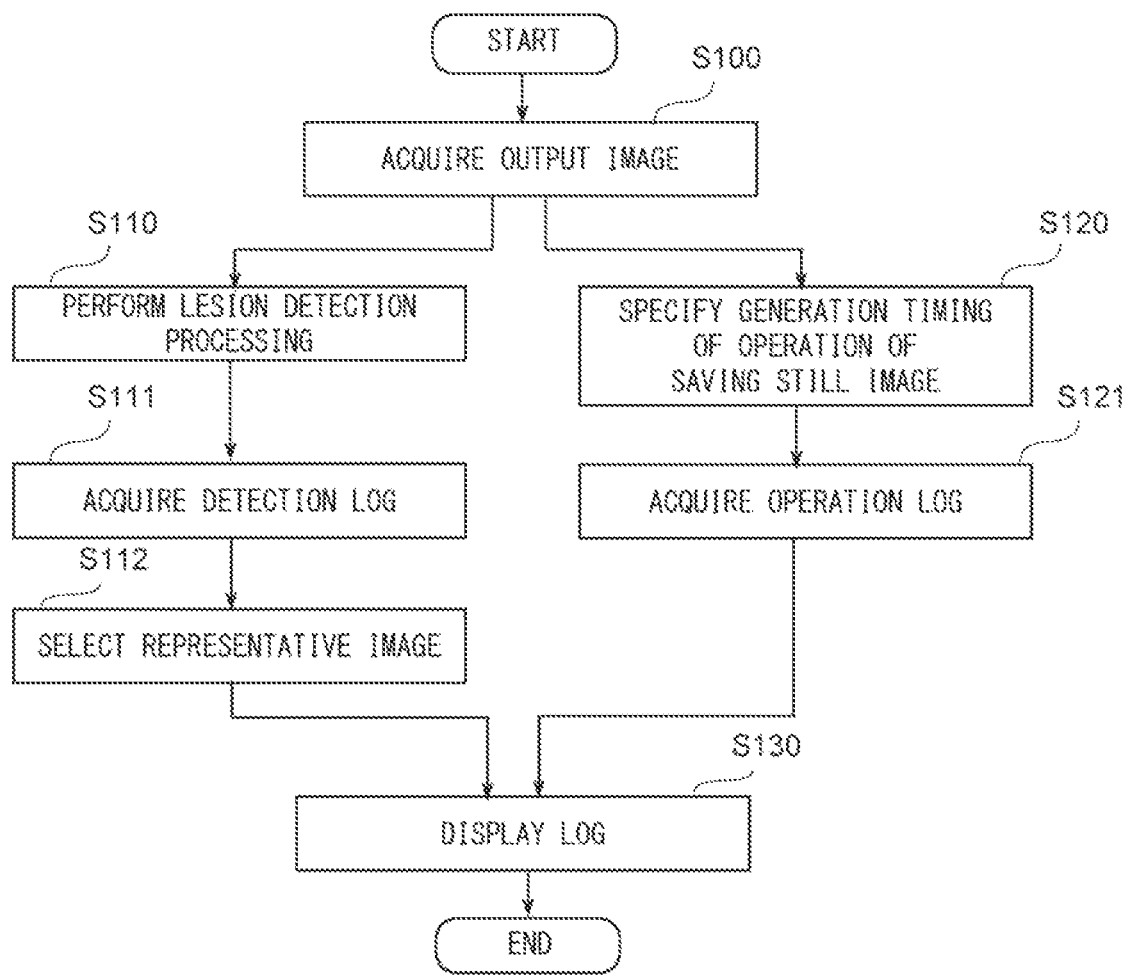
FIG. 9 is a flowchart showing an example of an operation of the information processing device according to the first example embodiment.

An operation example of the information processing device 200 will be described below. FIG. 9 is a flowchart showing an example of the operation of the information processing device 200. The operation example will be described below with reference to the flowchart of FIG. 9.

In step S100, the output image acquisition unit 210 acquires frame images constituting the captured moving image output by the processor device 130. After step S100, the process proceeds to steps S110 and S120. Processes from step S110 to step S112 and processes from step S120 to step S121 are performed in parallel, for example, but may be performed in order.

The processes from step S110 to step S112 will be described.

In step S110, the lesion detection unit 220 sequentially performs detection processing of a lesion site on the image acquired in step S110. The lesion detection unit 220 stores a log when the lesion site is detected.

Next, in step S111, the detection log acquisition unit 240 acquires the lesion image and capturing time information of the lesion image stored as the log.

Next, in step S112, the image selection unit 250 specifies a plurality of lesion images, in which the same lesion site is detected, with respect to the lesion image acquired in step S111, and selects a representative image from the plurality of specified lesion images. When the input/output control unit 260 does not display a summary of the plurality of lesion images in which the same lesion site is detected, such a step may be omitted.

The processes from step S120 to step S121 will be described.

In step S120, the operation log acquisition unit 230 analyzes the image acquired in step S100 to specify a timing at which the user has instructed to save. In other words, the operation log acquisition unit 230 specifies a generation timing of an operation of saving a still image (lesion image). Then, in step S121, the operation log acquisition unit 230 acquires a log related to the operation of the instruction to save performed during the examination. Specifically, the operation log acquisition unit 230 acquires, based on the timing specified in step S120, the capturing time of the lesion image instructed to be saved by the user and the lesion image.

After the processes of steps S112 and S121, the process proceeds to step S130. In step S130, the input/output control unit 260 displays the log on the display device 300.

The second example embodiment has been described above. According to the present embodiment, the capturing time of the lesion image instructed to be saved by the user during the examination with the endoscope and the capturing time of the lesion image of the lesion detected by the information processing device 200 are plotted on the time axis together with the lesion image. In other words, the capturing time of the lesion image of the lesion detected by the user and the capturing time of the lesion image of the lesion automatically detected are plotted on the time axis together with the lesion image. Therefore, both detection situations can be compared with each other on the time axis. Accordingly, it is possible to easily recognize the discrepancy between the detection result by the automatic detection processing and the detection result by the user.

Third Example Embodiment

A third example embodiment will be described below. For example, in the endoscopy of the large intestine, first, an endoscope 110 is inserted up to a beginning end side of the large intestine (an end side connected to the small intestine). Thereafter, substantive examination is started. In other words, observation is performed in order from the beginning end side of the large intestine toward a terminated end side of the large intestine (an end side connected to the anus) with the endoscope 110. In this way, after the position of the endoscope 110 reaches the start position of the examination, the actual examination is started. In other words, it is assumed that the user does not detect the lesion, that is, does not give an instruction to save the lesion image until the position of the endoscope 110 reaches the start position of the examination. On the other hand, the lesion detection unit 220 can also detect the lesion image from the image captured until the position of the endoscope 110 reaches the start position of the examination. However, as described above, since the actual examination of the user is performed after the position of the endoscope 110 reaches the start position of the examination, the advantage of displaying the log on the display device 300 until the position of the endoscope 110 reaches the start position of the examination is insufficient.

Therefore, in the present embodiment, a description will be given with respect to a configuration in which the log after the position of the endoscope 110 reaches the start position of the examination is displayed on the display device 300.

Hereinafter, differences from the second example embodiment will be described, and duplicated descriptions will not be made. In the present embodiment, an information processing device 201 is used instead of the information processing device 200.

Figure 10:
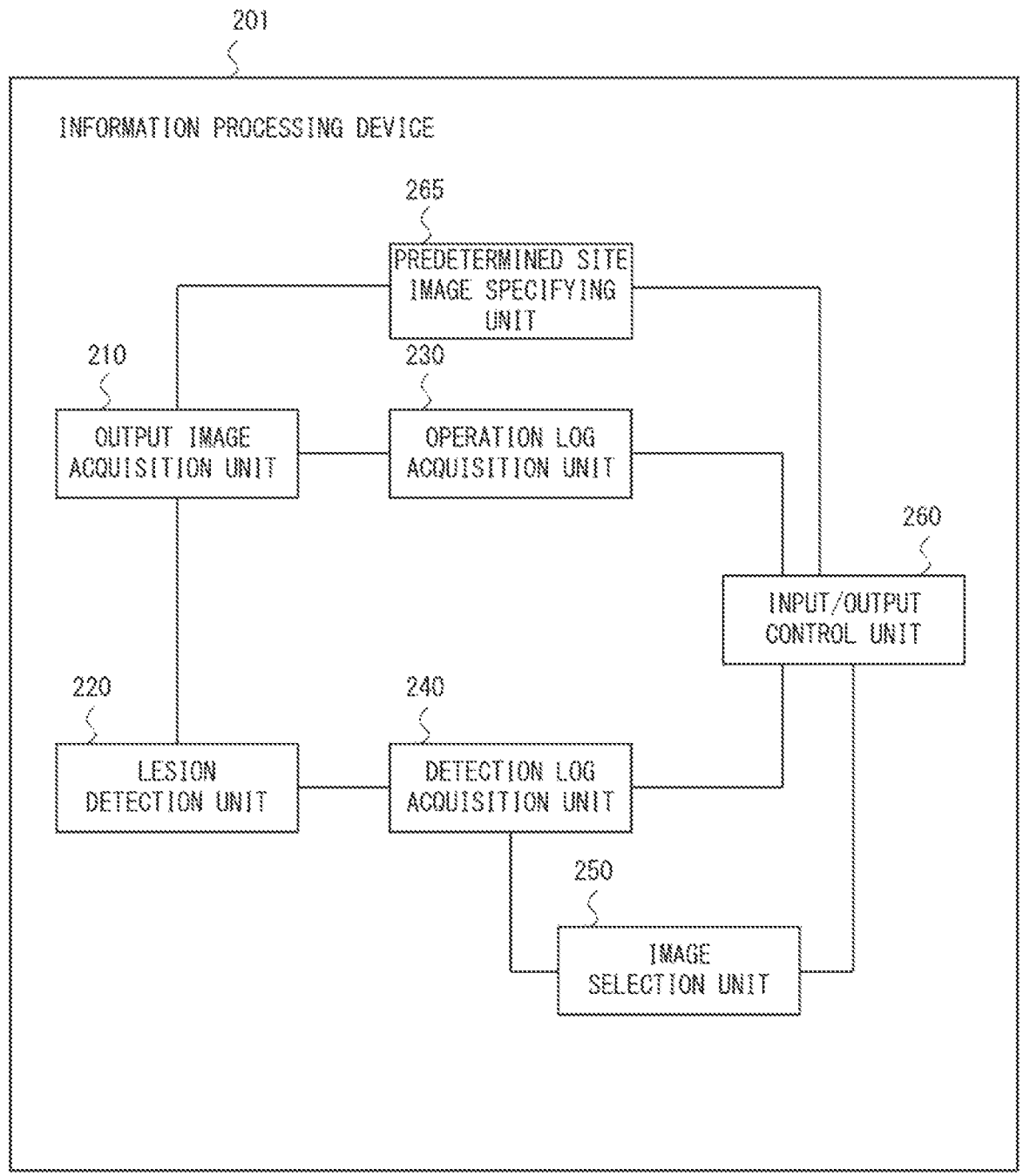
FIG. 10 is a block diagram showing an example of a functional configuration of an information processing device according to a third example embodiment.

FIG. 10 is a block diagram showing an example of a functional configuration of the information processing device 201 according to the third example embodiment. As shown in FIG. 10, the information processing device 201 differs from the information processing device 200 according to the second example embodiment in that a predetermined site image specifying unit 265 is further provided. Processing of the predetermined site image specifying unit 265 is realized when the processor 292 reads and executes software (computer program) from the memory 291, for example.

The predetermined site image specifying unit 265 specifies an image, in which a predetermined site in the body cavity is captured, from a series of images captured by the endoscope 110 during the examination with the endoscope 110. For example, in the case of endoscopy of the large intestine, the predetermined site may be a site existing on the beginning end side of the large intestine. In this case, specifically, the predetermined site may be, for example, an ileocecal valve, or an entrance portion of the appendix. These sites are merely example, and the predetermined site may be a site near the start position of the examination. The predetermined site image specifying unit 265 performs the known image recognition processing on the image captured by the endoscope 110, and specifies the image in which the predetermined site is captured. For example, the predetermined site image specifying unit 265 inputs an image to the model learned in advance by a machine learning algorithm to determine whether the image is an image in which the predetermined site is captured. Such a model is, for example, a model learned by deep learning such as CNN, but may be a model learned using another machine learning algorithm.

The input/output control unit 260 of the present embodiment displays, as a display target, the log after the capturing time of the image in which the predetermined site is captured. In other words, the input/output control unit 260 plots the capturing time after the capturing time of the image in which the predetermined site is captured on the time axis 62. Similarly, the input/output control unit 260 displays a lesion image captured after the capturing time of the image in which the predetermined site is captured. In other words, the input/output control unit 260 excludes the logs (that is, the capturing time of the lesion image and the lesion image) up to the capturing time of the image in which the predetermined site is captured from the display target. As described above, it is assumed that the user does not give an instruction to save the lesion image until the position of the endoscope 110 reaches the start position of the examination, but the lesion detection unit 220 can detect the lesion image regardless of whether the position of the endoscope 110 has reached the start position of the examination. Therefore, the input/output control unit 260 preferably restricts the display of the log of the detection processing by the lesion detection unit 220 as described above.

Figure 11:
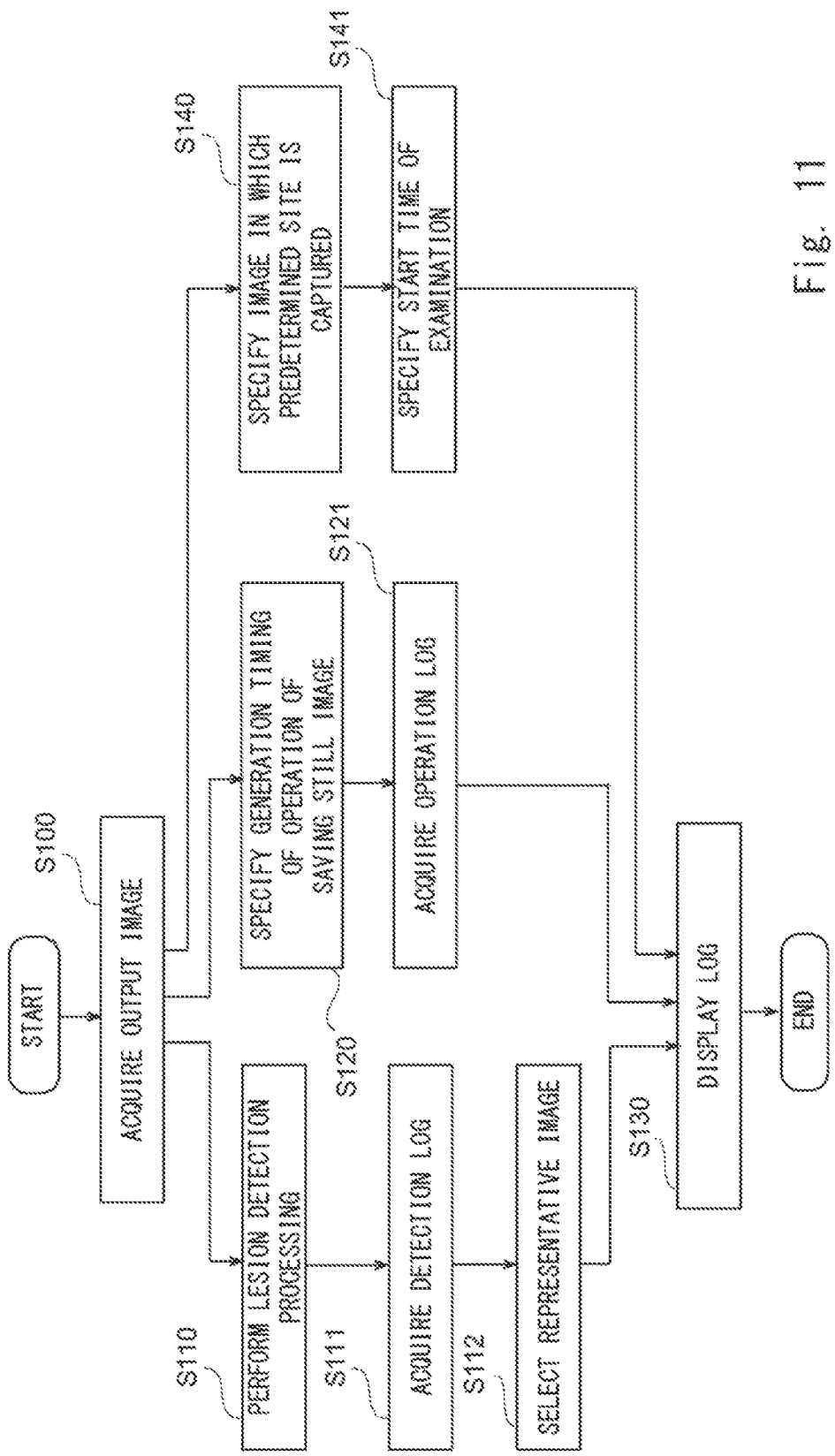
FIG. 11 is a flowchart showing an example of an operation of the information processing device according to the third example embodiment.

An operation example of the information processing device 201 will be described below. FIG. 11 is a flowchart showing an example of the operation of the information processing device 201. The flowchart shown in FIG. 11 differs from the flowchart shown in FIG. 9 in that steps S140 and S141 are added. Differences from the flowchart shown in FIG. 9 will be described.

The information processing device 201 further performs processes of steps S140 and S141 after the process of step S100. Processes from step S110 to step S112, processes from step S120 to step S121, and processes from step S140 to step S141 are performed in parallel, for example, but may be performed in order.

In step S140, the predetermined site image specifying unit 265 specifies an image, in which a predetermined site is captured, from a series of images captured by the endoscope 110 during the examination with the endoscope 110.

Next, in step S141, the input/output control unit 260 specifies an actual start time of the examination based on the processing result in step S140. In other words, the input/output control unit 260 sets the capturing time of the image, in which the predetermined site is captured, as the actual start time of the examination.

Then, in step S130, the input/output control unit 260 displays, as a display target, the log after the time specified in step S141.

The third example embodiment has been described above. According to the present embodiment, the information processing device 201 displays, as the display target, the log after the time when the predetermined site is captured. Therefore, only the log after the position of the endoscope 110 reaches the start position of the actual examination can be displayed. In other words, it is possible to prevent the display of the log before the start of the actual examination. Therefore, the visibility of the display of the log of the actual examination can be improved.

Fourth Example Embodiment

A fourth example embodiment will be described below. In the above-described embodiments, the discrepancy between the detection result by the detection processing on the captured image of the endoscope 110 and the detection result by the user is found by the user who has seen the display of the display device 300. In the present embodiment, a configuration for automatically detecting such discrepancy will be described.

Hereinafter, differences from the second example embodiment will be described, and duplicated descriptions will not be made. In the present embodiment, an information processing device 202 is used instead of the information processing device 200.

Figure 12:
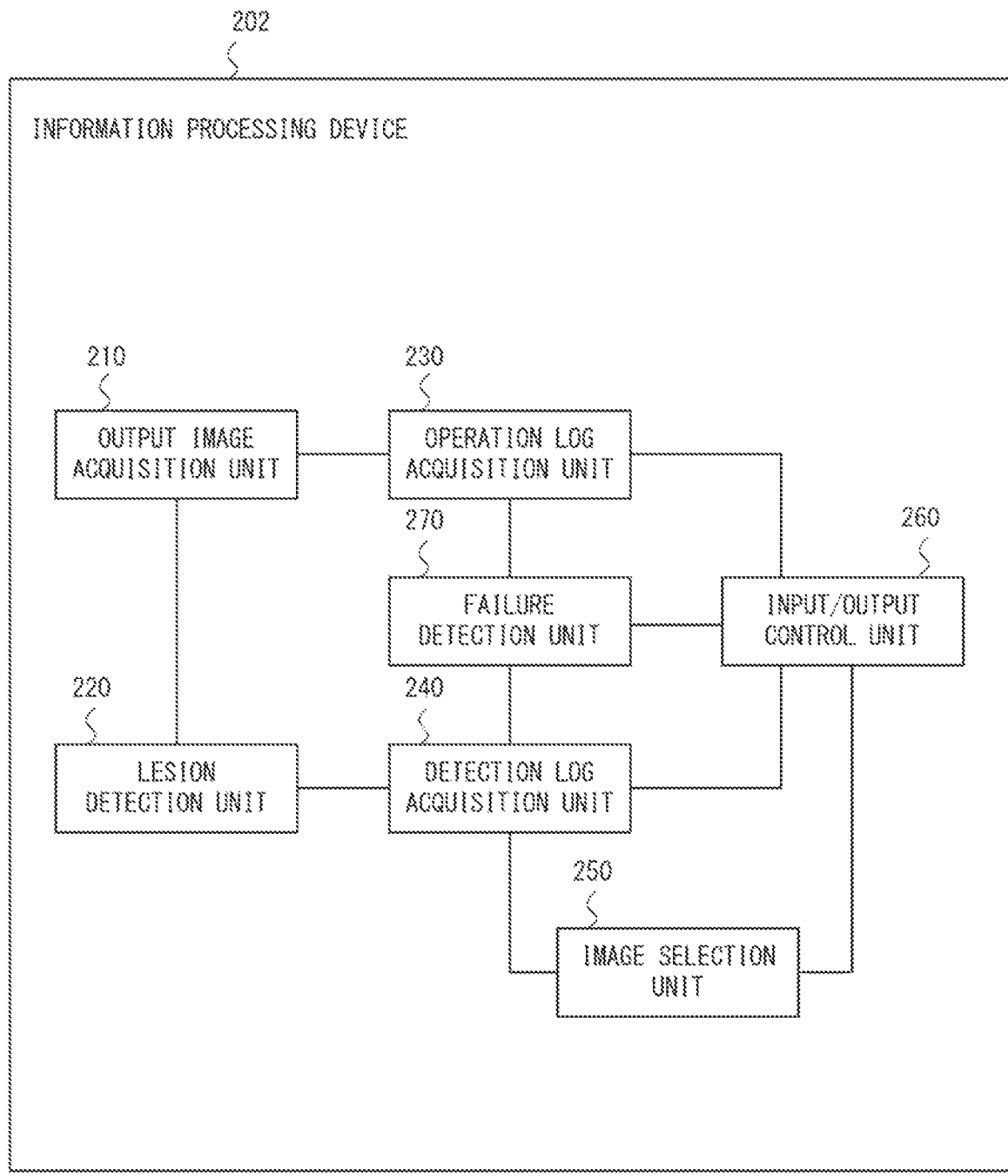
FIG. 12 is a block diagram showing an example of a functional configuration of an information processing device according to a fourth example embodiment.

FIG. 12 is a block diagram showing an example of a functional configuration of the information processing device 202 according to the fourth example embodiment. As shown in FIG. 12, the information processing device 202 differs from the information processing device 200 according to the second example embodiment in that a failure detection unit 270 is further provided. Processing of the failure detection unit 270 is realized when the processor 292 reads and executes software (computer program) from the memory 291, for example.

The failure detection unit 270 detects a failure of detection of a lesion site by the user or the detection processing. In other words, the failure detection unit 270 detects a failure of detection of the lesion site by the user during the examination with the endoscope 110, or a failure of detection of the lesion site by the lesion detection unit 220. Here, the failure of detection includes a failure due to omission of detection of the lesion site and a failure due to erroneous detection of a normal site as a lesion site (that is, a failure due to erroneous detection). The failure detection unit 270 detects a failure by checking a corresponding relation between the log acquired by the operation log acquisition unit 230 and the log acquired by the detection log acquisition unit 240. The failure detected by the failure detection unit 270 may not actually be a failure. Therefore, it can be said that the failure detection unit 270 has detected failure candidates.

The failure detection unit 270 of the present embodiment detects the failure of detection of the lesion site by the user or the detection processing by comparing the lesion image acquired by the operation log acquisition unit 230 with the lesion image acquired by the detection log acquisition unit 240. Specifically, the failure detection unit 270 determines whether the detection log acquisition unit 240 acquires a lesion image depicted with the same lesion site as the lesion site depicted in the lesion image acquired by the operation log acquisition unit 230. Similarly, the failure detection unit 270 determines whether the operation log acquisition unit 230 acquires a lesion image depicted with the same lesion site as the lesion site depicted in the lesion image acquired by the detection log acquisition unit 240. The failure detection unit 270 calculates, for example, similarity between the lesion image acquired by the operation log acquisition unit 230 and the lesion image acquired by the detection log acquisition unit 240, and thus determines whether the lesion site depicted in one lesion image is depicted in the other lesion image.

When the detection log acquisition unit 240 does not acquire the lesion image depicted with the same lesion site as the lesion site depicted in the lesion image acquired by the operation log acquisition unit 230, there is a possibility that omission of detection by the lesion detection unit 220 or erroneous detection by the user has occurred. Therefore, the failure detection unit 270 detects the failure of detection of the lesion site when the detection log acquisition unit 240 does not acquire the lesion image depicted with the same lesion site as the lesion site depicted in the lesion image acquired by the operation log acquisition unit 230. In other words, the failure detection unit 270 detects that a failure has occurred in the lesion image depicted with the lesion site.

Further, when the operation log acquisition unit 230 does not acquire the lesion image depicted with the same lesion site as the lesion site depicted in the lesion image acquired by the detection log acquisition unit 240, there is a possibility that omission of detection by the user or erroneous detection by the lesion detection unit 220 has occurred. Therefore, the failure detection unit 270 detects the failure of detection of the lesion site when the operation log acquisition unit 230 does not acquire the lesion image depicted with the same lesion site as the lesion site depicted in the lesion image acquired by the detection log acquisition unit 240. In other words, the failure detection unit 270 detects that a failure has occurred in the lesion image depicted with the lesion site.

Figure 13:
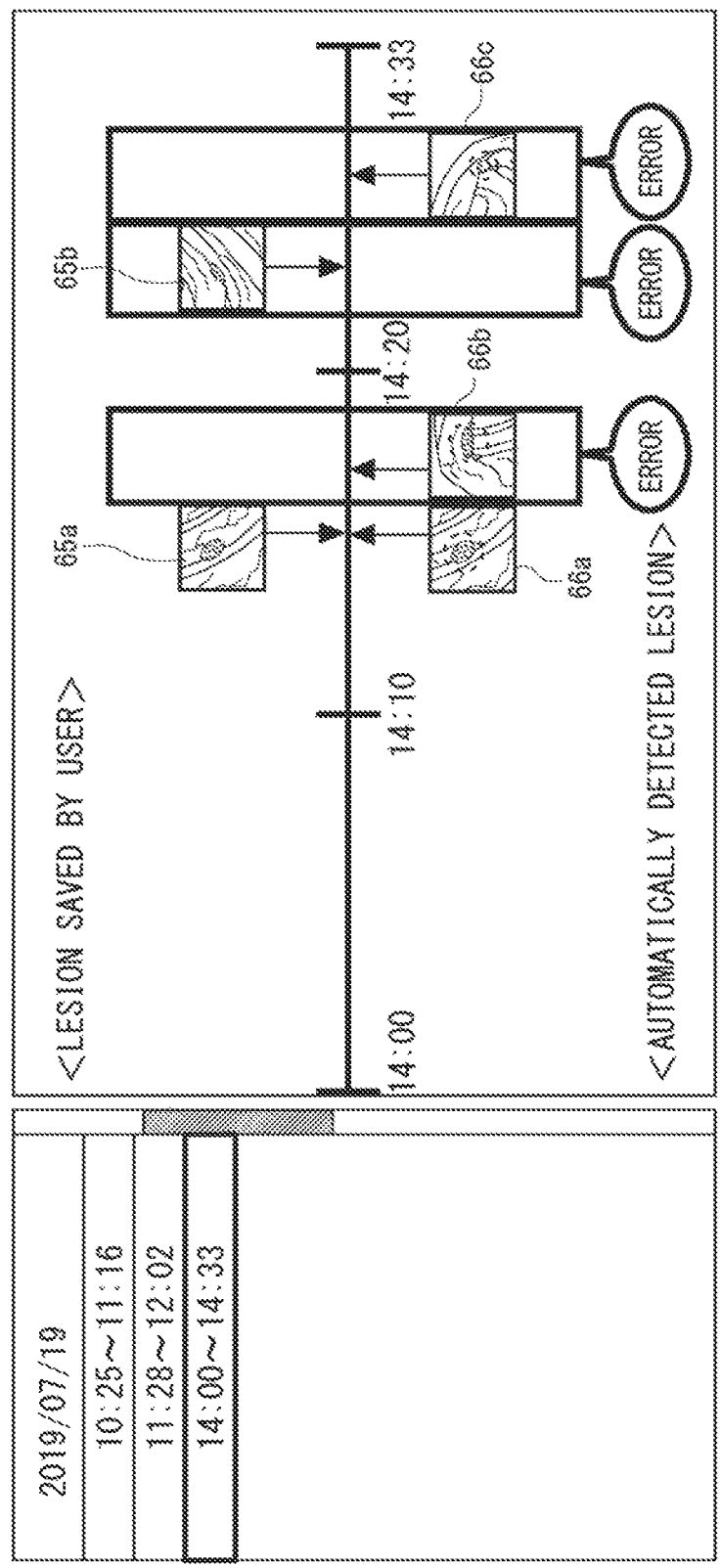
FIG. 13 is a schematic diagram showing a display example when a failure detection unit detects a failure.

When the failure detection unit 270 detects the failure, the input/output control unit 260 of the present embodiment displays a display indicating which lesion image the failure has been detected. FIG. 13 shows a display example of the display device 300 when the failure detection unit 270 detects a failure. In the example shown in FIG. 13, it is displayed that failures have been detected with respect to a lesion image 66b, a lesion image 65b, and a lesion image 66c.

In the above description, the failure detection unit 270 detects the failure by comparing the lesion images, but the failure detection unit 270 may detect the failure by comparing the capturing times. For example, the failure detection unit 270 may detect the failure of detection of the lesion site by the user or the detection processing by comparing the capturing time acquired by the operation log acquisition unit 230 with the capturing time acquired by the detection log acquisition unit 240. In other words, the failure detection unit 270 may detect the failure by comparing the capturing time of the lesion image instructed to be saved by the user with the capturing time of the lesion image detected by the detection processing. Specifically, the failure detection unit 270 checks whether only any one of the capturing time of the lesion image instructed to be saved by the user and the capturing time of the lesion image detected by the detection processing is not acquired every predetermined unit time.

When only the capturing time of the lesion image instructed to be saved by the user is acquired in the unit time of the check target, there is a possibility that omission of detection by the lesion detection unit 220 or erroneous detection by the user may occur. Accordingly, in this case, the failure detection unit 270 detects the failure of detection of the lesion site captured in the unit time. In addition, when only the capturing time of the lesion image detected by the detection processing is acquired in the unit time of the check target, there is a possibility that omission of detection by the user or erroneous detection by the lesion detection unit 220 may occur. Accordingly, in this case, the failure detection unit 270 detects the failure of detection of the lesion site captured in the unit time. When the failure detection unit 270 detects the failure by comparing the capturing times, the input/output control unit 260 may display a display indicating which capturing time the failure has been detected.

In this way, the lesion detection unit 220 may detect the failure by comparing the lesion images, or may detect the failure by comparing the capturing times. However, it is preferable to detect the failure by comparing the lesion images from the following reasons. In the case of comparing the capturing times, even when the user and the lesion detection unit 220 appropriately detect the same lesion site, it will be determined that the failure of detection has occurred when there is no temporal corresponding relation between the lesion images. On the other hand, in the case of comparing the lesion images, since the image contents are compared with each other, the occurrence of such a determination result can be prevented.

Figure 14:
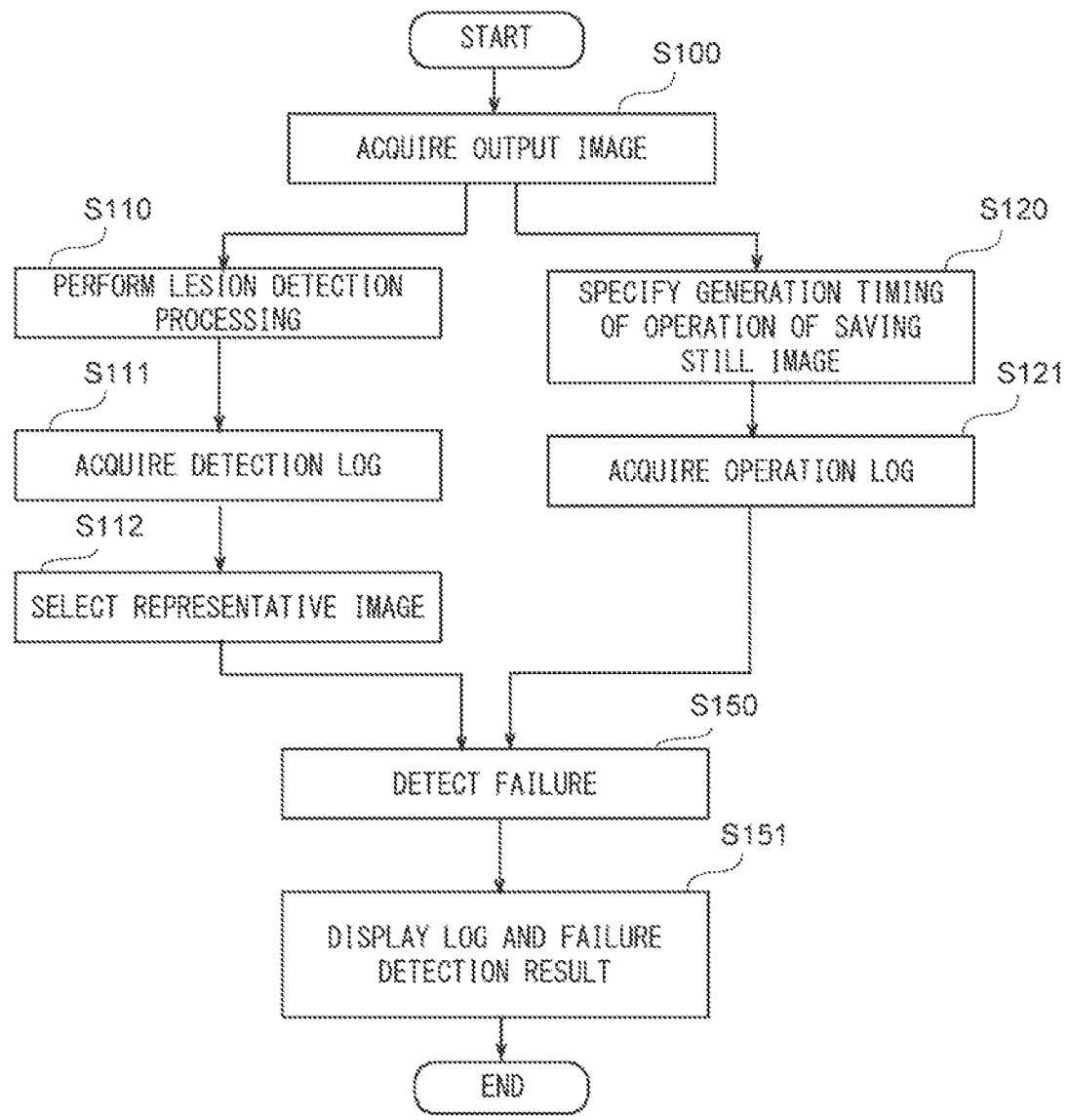
FIG. 14 is a flowchart showing an example of an operation of the information processing device according to the fourth example embodiment.

An operation example of the information processing device 202 will be described below. FIG. 14 is a flowchart showing an example of the operation of the information processing device 202. The flowchart shown in FIG. 14 differs from the flowchart shown in FIG. 9 in that step S150 is added and step S130 is replaced with step S151. Differences from the flowchart shown in FIG. 9 will be described below.

In the flowchart shown in FIG. 14, after processes of steps S112 and S121, the process proceeds to step S150. In step S150, the failure detection unit 270 detects the failure of detection of the lesion site by the user or the detection processing by checking a corresponding relation between the log acquired by the operation log acquisition unit 230 and the log acquired by the detection log acquisition unit 240. After step S150, the process proceeds to step S151. In step S151, the input/output control unit 260 displays the log and the failure detection result on the display device 300.

The fourth example embodiment has been described above. According to the present embodiment, the failure of detection of the lesion site is detected by checking the corresponding relation between the log acquired by the operation log acquisition unit 230 and the log acquired by the detection log acquisition unit 240. For this reason, the user can more easily grasp the discrepancy between the detection result by the detection processing on the captured image of the endoscope 110 and the detection result by the user.

Fifth Example Embodiment

A fifth example embodiment will be described below. In the present embodiment, a configuration will be described in which feedback data is generated to improve detection accuracy of the lesion detection unit 220.

Hereinafter, differences from the second example embodiment will be described, and duplicated descriptions will not be made. In the present embodiment, an information processing device 203 is used instead of the information processing device 200.

Figure 15:
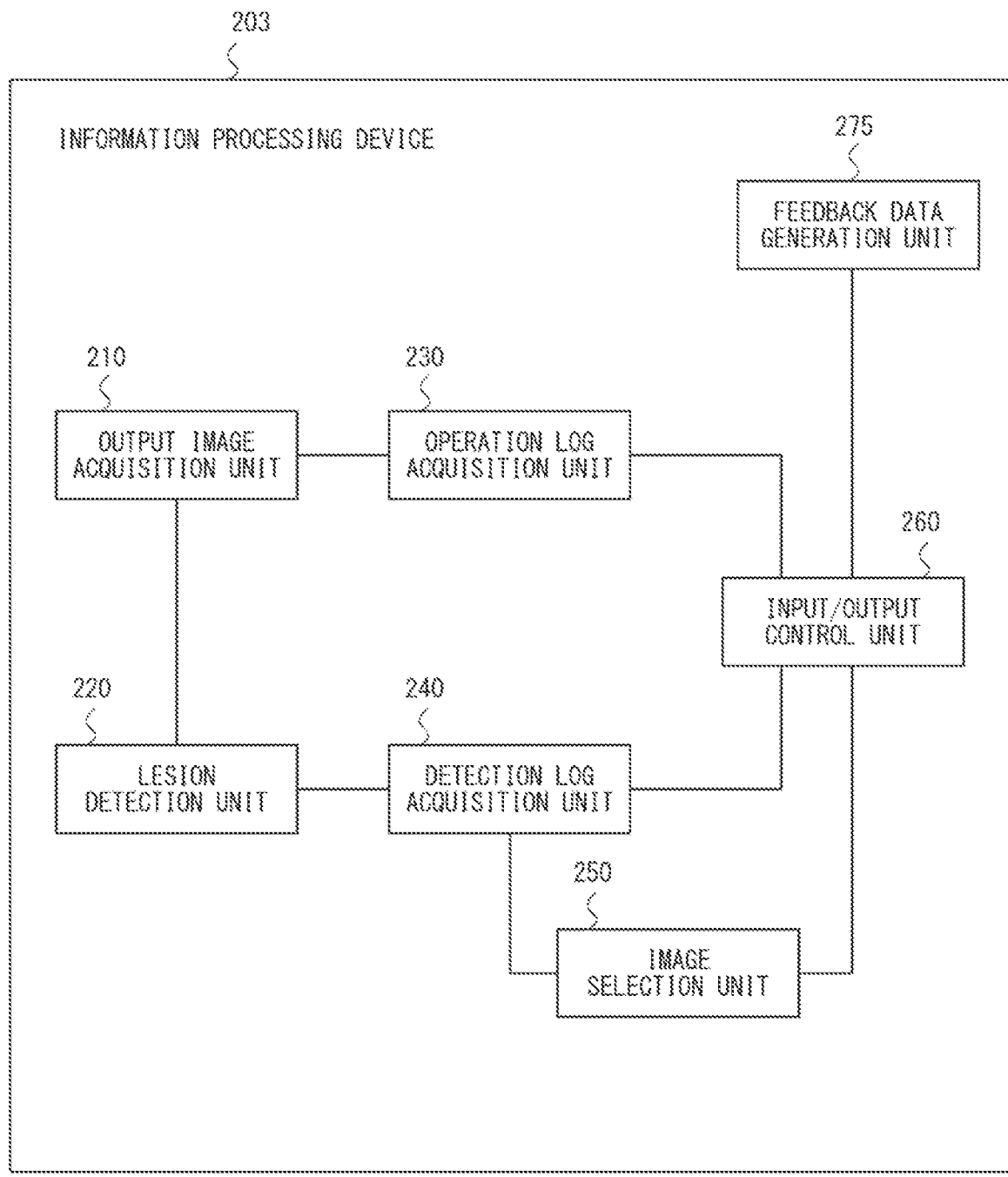
FIG. 15 is a block diagram showing an example of a functional configuration of an information processing device according to a fifth example embodiment.

FIG. 15 is a block diagram showing an example of a functional configuration of the information processing device 203 according to the fifth example embodiment. As shown in FIG. 15, the information processing device 203 differs from the information processing device 200 according to the second example embodiment in that a feedback data generation unit 275 is further provided. Processing of the feedback data generation unit 275 is realized when the processor 292 reads and executes software (computer program) from the memory 291, for example.

The feedback data generation unit 275 generates feedback data based on the information input from the user. Specifically, the feedback data generation unit 275 generates, as feedback data, data in which the lesion image is associated with detection failure information. Here, detection failure information is analysis information about the failure of detection by the lesion detection unit 220, and includes the type of detection failure (failure due to detection omission of the lesion or failure due to erroneous detection of the lesion) and the cause of the failure. However, the detection failure information may not necessarily have to include the cause of the failure. The feedback data generation unit 275 generates feedback data based on the instruction to select the lesion image input from the user and the detection failure information on the selected lesion image input from the user.

In the present embodiment, the input/output control unit 260 further provides a user interface for generating feedback data. In other words, the input/output control unit 260 performs processing of receiving the instruction to select the lesion image as an input and processing of receiving the detection failure information on the selected lesion image as an input. In addition, the input/output control unit 260 displays a screen for such processing.

Figure 16:
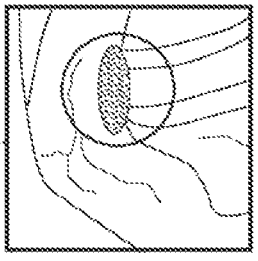
FIG. 16 is a schematic diagram showing a display example of a screen to be displayed for generation of feedback data.
Figure 17:
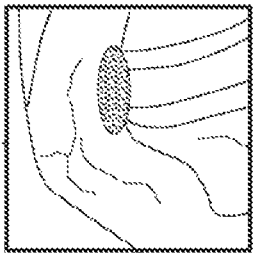
FIG. 17 is a schematic diagram showing a display example of a screen to be displayed for generation of feedback data.

FIGS. 16 and 17 are schematic diagrams showing a display example of a screen displayed on the display device 300 for generating feedback data. The input/output control unit 260 performs display for inputting the detection failure information in a failure information area 70 on the screen of the display device 300. The input/output control unit 260 displays a screen to input the detection failure information when receiving an input from the user to select one of the lesion images displayed on the log display screen shown in FIG. 5. The selection of the lesion image may be a selection of the lesion image acquired by the detection log acquisition unit 240, or may be a selection of the lesion image acquired by the operation log acquisition unit 230. For example, the lesion image is selected when the user performs an operation of touching (tapping) or clicking of any lesion image.

In the failure information area 70, a selected lesion image 71 is displayed, and an input field 72 of the detection failure information is displayed. The input field 72 includes a type input field 721 which is an input field for the type of detection failure and a cause input field 722 which is an input field for the cause of the detection failure. The user looks at the lesion image 71 and inputs the detection failure information. For example, the user selects an appropriate type of detection failure from options, and selects an appropriate cause of the failure from the options.

FIG. 16 shows an example of an input screen of detection failure information on the lesion image depicted with a lesion erroneously detected by the lesion detection unit 220. In the example shown in FIG. 16, examples of options for the cause of erroneous detection include erroneous detection due to reflection of an instrument, erroneous detection due to blurring of the captured image, erroneous detection due to detection of bubbles as a lesion, and erroneous detection due to a captured image which is too darkened.

FIG. 17 shows an example of an input screen of detection failure information on the lesion image depicted with a lesion detected by the user although the detection is overlooked by the lesion detection unit 220. In FIG. 17, examples of options for the cause of detection omission include detection omission due to reflection of the instrument, detection omission due to blurring of the captured image, detection omission due to reflection of bubbles or the like, and detection omission due to a flat lesion that is presumed to make detection difficult.

The feedback data generation unit 275 generates, as feedback data, data in which the selected lesion image and the input detection failure information are associated with each other. Even for a lesion image similar to the selected lesion image, the feedback data generation unit 275 may generate feedback data associated with the detection failure information input for the selected lesion image. The feedback data generation unit 275 may store the generated feedback data in the storage device such as the memory 291, or may provide the generated feedback data to another device. Further, the input/output control unit 260 may display the generated feedback data as a history on the display device 300.

Figure 18:
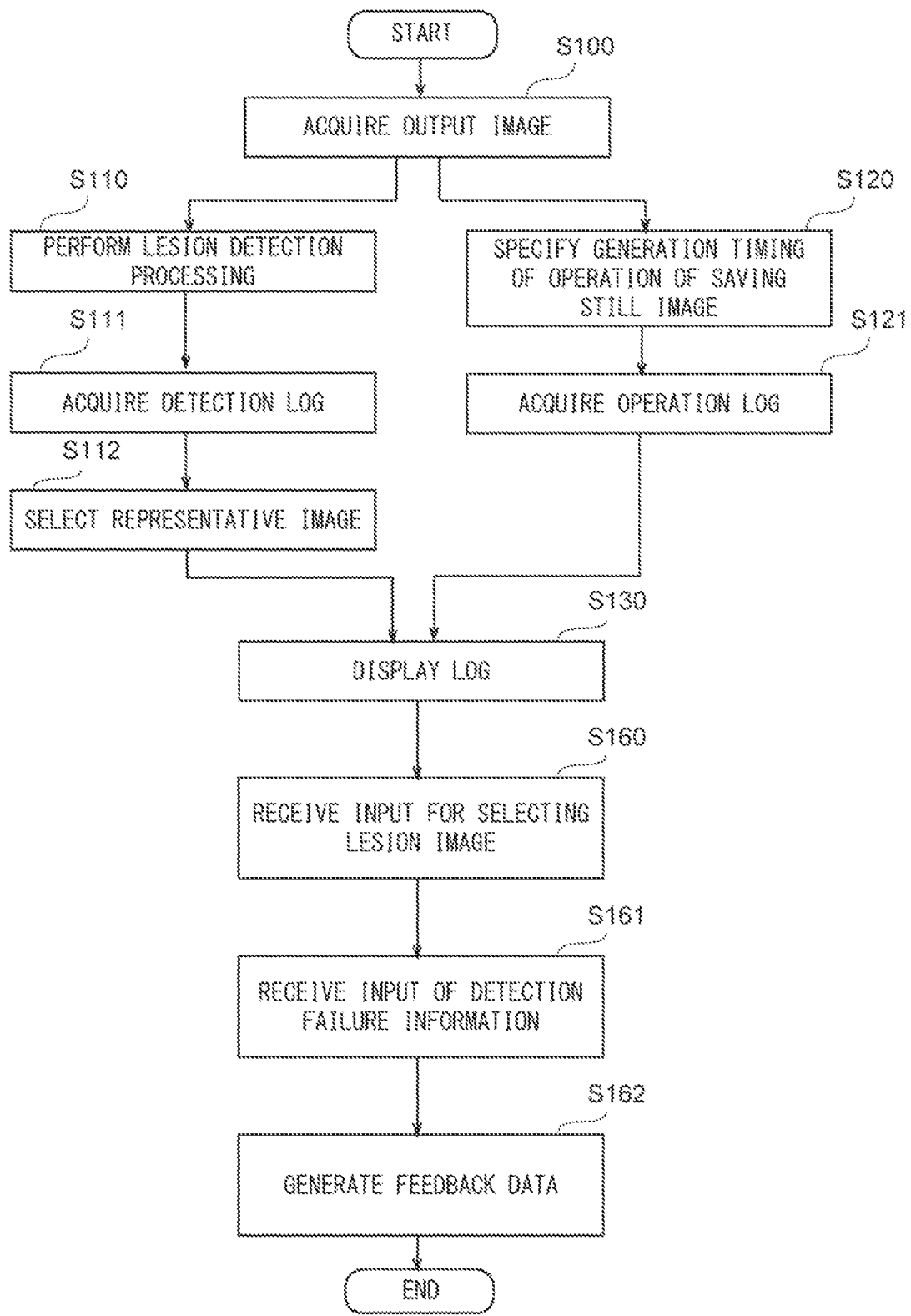
FIG. 18 is a flowchart showing an example of an operation of the information processing device according to the fifth example embodiment.

An operation example of the information processing device 203 will be described below. FIG. 18 is a flowchart showing an example of the operation of the information processing device 203. The flowchart shown in FIG. 18 differs from the flowchart shown in FIG. 9 in that steps S160 to S162 are added. Differences from the flowchart shown in FIG. 9 will be described.

In the flowchart shown in FIG. 18, after a process of step S130, the process proceeds to step S160. In step S160, the input/output control unit 260 receives an input for selecting a lesion image. Then, the input/output control unit 260 displays the above-described input screen of the detection failure information.

Next, in step S161, the input/output control unit 260 receives an input of the detection failure information. Then, in step S162, the feedback data generation unit 275 generates feedback data based on the inputs received in steps S160 and S161.

The fifth example embodiment has been described above. According to the present embodiment, the feedback data about the failure of detection by the lesion detection unit 220 is generated. Therefore, it is possible to obtain data useful for improving the accuracy of the detection processing of the lesion detection unit 220.

Various modifications can be considered for each of the above-described example embodiments. For example, in the above-described example embodiments, the output image acquisition unit 210 acquires the captured image from the processor device 130 in real time, and the lesion detection unit 220 performs the detection processing of the lesion in real time, but these processing may not be performed in real time. In the above-described example embodiments, each of the information processing devices 200, 201, 202, and 203 includes the lesion detection unit 220, but since each of the information processing devices 200, 201, 202, and 203 only needs to be able to acquire the log of the detection processing, the lesion detection unit 220 may be provided in another device. In this case, the detection log acquisition unit 240 acquires the log of the detection processing from another device. Further, the features of the above-described second to fifth example embodiments may be arbitrarily combined. In the above-described example embodiments, the examination support system 10 includes the display device 140 and the display device 300, but all the displays may be performed on any one of the display devices.

Although the present invention is described above with reference to the example embodiments, the present invention is not limited to the above-described example embodiments. Various modifications that can be understood by those skilled in the art can be made to the configuration and details of the present invention within the scope of the present invention.

Some or all of the above-described example embodiments may also be described as in the following supplementary notes, but are not limited to the following.

Supplementary Note 1

An information processing device comprising:
a first acquisition unit configured to acquire a capturing time of a lesion image instructed to be saved by a user, from a series of images captured by an endoscope during examination with the endoscope;
a second acquisition unit configured to acquire a capturing time of a lesion image detected by detection processing for the series of images captured by the endoscope during the examination; and
a display control unit configured to cause a display device to display a first capturing time and a second capturing time which are plotted on a time axis, the first capturing time being the capturing time acquired by the first acquisition unit, the second capturing time being the capturing time acquired by the second acquisition unit.

Supplementary Note 2

The information processing device according to Supplementary note 1, wherein
the first acquisition unit further acquires a first lesion image that is the lesion image instructed to be saved by the user,
the second acquisition unit further acquires a second lesion image that is the lesion image detected by the detection processing, and
the display control unit displays the first lesion image in association with the first capturing time, and displays the second lesion image in association with the second capturing time.

Supplementary Note 3

The information processing device according to Supplementary note 2, further comprising an image selection unit configured to specify a plurality of the second lesion images in which the same lesion site is detected and to select a representative image from the plurality of the second lesion images,
wherein the display control unit displays the second lesion image selected as the representative image from the plurality of the second lesion images in which the same lesion site is detected.

Supplementary Note 4

The information processing device according to Supplementary note 2 or 3, further comprising a feedback data generation unit configured to, based on an instruction to select the first lesion image or the second lesion image input from the user and detection failure information of the selected lesion image input from the user, generate feedback data in which the lesion image and the detection failure information are associated with each other,
wherein the detection failure information is information indicating, as a type of detection failure, either of erroneous detection of a lesion and detection omission of a lesion.

Supplementary Note 5

The information processing device according to any one of Supplementary notes 1 to 4, further comprising a predetermined site image specifying unit configured to specify, from the series of images, an image in which a predetermined site of a body cavity is captured,
wherein the display control unit plots the second capturing time after a capturing time of the image in which the predetermined site is captured, on the time axis.

Supplementary Note 6

The information processing device according to Supplementary note 2, further comprising an output image acquisition unit configured to acquire the series of images output from an image output device configured to output the image captured by the endoscope, wherein
the image output device is a device configured to output an image having a predetermined feature until a certain time elapses from an instruction time when the user instructs to save a lesion image during the examination with the endoscope,
the first acquisition unit acquires the capturing time of the lesion image instructed to be saved by the user and the lesion image by determining a time when an instruction to save is generated based on the presence or absence of the feature in the image acquired by the output image acquisition unit.

Supplementary Note 7

The information processing device according to any one of Supplementary notes 1 to 6, wherein the display control unit displays a scale of the time axis in an enlarged or reduced manner, based on the instruction input from the user.

Supplementary Note 8

The information processing device according to any one of Supplementary notes 1 to 7, wherein
the first acquisition unit further acquires a first lesion image which is the lesion image instructed to be saved by the user,
the second acquisition unit further acquires a second lesion image which is the lesion image detected by the detection processing, and
the information processing device further includes a failure detection unit configured to detect a failure of detection of a lesion site by the user or the detection processing by comparing the first lesion image with the second lesion image.

Supplementary Note 9

The information processing device according to any one of Supplementary notes 1 to 7, further comprising a failure detection unit configured to detect a failure of detection of a lesion site by the user or the detection processing by comparing the first capturing time with the second capturing time.

Supplementary Note 10

A display method comprising:
acquiring a capturing time of a lesion image instructed to be saved by a user, from a series of images captured by an endoscope during examination with the endoscope;

acquiring a capturing time of a lesion image detected by detection processing for the series of images captured by the endoscope during the examination; and causing a display device to display a first capturing time and a second capturing time which are plotted on a time axis, the first capturing time being the capturing time of the lesion image instructed to be saved by the user, the second capturing time being the capturing time of the lesion image detected by the detection processing.

Supplementary Note 11

A non-transitory computer-readable medium storing a program that causes a computer to execute:
- a first acquisition step of acquiring a capturing time of a lesion image instructed to be saved by a user, from a series of images captured by an endoscope during examination with the endoscope;
- a second acquisition step of acquiring a capturing time of a lesion image detected by detection processing for the series of images captured by the endoscope during the examination; and
- a display control step of causing a display device to display a first capturing time and a second capturing time which are plotted on a time axis, the first capturing time being the capturing time acquired in the first acquisition step, the second capturing time being the capturing time acquired in the second acquisition step.

REFERENCE SIGNS LIST

1 INFORMATION PROCESSING DEVICE
2 FIRST ACQUISITION UNIT
3 SECOND ACQUISITION UNIT
4 DISPLAY CONTROL UNIT
10 EXAMINATION SUPPORT SYSTEM
62 TIME AXIS
63 MARK
64 MARK
100 ENDOSCOPE SYSTEM
110 ENDOSCOPE
111 INSERTION PORTION
112 OPERATION PORTION
113 IMAGE CAPTURING PORTION
120 LIGHT SOURCE DEVICE
130 PROCESSOR DEVICE
140 DISPLAY DEVICE
200 INFORMATION PROCESSING DEVICE
201 INFORMATION PROCESSING DEVICE
202 INFORMATION PROCESSING DEVICE
203 INFORMATION PROCESSING DEVICE
210 OUTPUT IMAGE ACQUISITION UNIT
220 LESION DETECTION UNIT
230 OPERATION LOG ACQUISITION UNIT
240 DETECTION LOG ACQUISITION UNIT
250 IMAGE SELECTION UNIT
260 INPUT/OUTPUT CONTROL UNIT
265 PREDETERMINED SITE IMAGE SPECIFYING UNIT
270 FAILURE DETECTION UNIT
275 FEEDBACK DATA GENERATION UNIT
300 DISPLAY DEVICE

The invention claimed is:

1. An information processing device comprising:
at least one first memory storing program instructions; and
at least one first processor configured to execute the instructions stored in the first memory to:
acquire a first capturing time and a first lesion image of a lesion image instructed to be saved by a user, from a series of images captured by an endoscope during examination with the endoscope;
acquire a second capturing time and a second lesion image of a lesion image detected by detection processing for the series of images captured by the endoscope during the examination;
perform control so as to display the first lesion image in association with the first capturing time, and display the second lesion image in association with the second capturing time;
display a position in the second lesion image of a lesion site detected by the detection processing; and
based on an instruction to select the first lesion image or the second lesion image input from the user and detection failure information of the selected lesion image input from the user, generate feedback data in which the lesion image and the detection failure information are associated with each other, the feedback data being data for improving detection accuracy of the detection processing, wherein
the detection failure information includes information indicating the lesion image depicted with a lesion detected by the user although the detection is overlooked by the detection processing.

2. The information processing device according to claim 1, wherein the first processor is further configured to execute the instructions to:
specify a plurality of the second lesion images in which the same lesion site is detected,
select a representative image from the plurality of the second lesion images, and
perform control so as to display the second lesion image selected as the representative image from the plurality of the second lesion images in which the same lesion site is detected.

3. The information processing device according to claim 1, wherein the first processor is further configured to execute the instructions to:
specify, from the series of images, an image in which a predetermined site of a body cavity is captured, and
perform control so as to plot the second capturing time after a capturing time of the image in which the predetermined site is captured, on the time axis.

4. The information processing device according to claim 1, wherein
the first processor is further configured to execute the instructions to acquire the series of images output from an image output device configured to output the image captured by the endoscope,
the image output device comprises at least one second memory storing program instructions and at least one second processor configured to execute the instructions stored in the second memory to output an image having a predetermined feature until a certain time elapses from an instruction time when the user instructs to save the lesion image during the examination with the endoscope, and
the first processor is further configured to execute the instructions to acquire the first capturing time of the lesion image instructed to be saved by the user and the first lesion image by determining a time when an instruction to save is generated based on the presence or absence of the feature in the image acquired from the image output device.

5. The information processing device according to claim 1, wherein the first processor is further configured to execute the instructions to perform control so as to display a scale of the time axis in an enlarged or reduced manner, based on the instruction input from the user.

6. The information processing device according to claim 1, wherein the first processor is further configured to execute the instructions to:
   detect a failure of detection of a lesion site by the user or the detection processing by comparing the first lesion image with the second lesion image.

7. The information processing device according to claim 1, wherein the first processor is further configured to execute the instructions to detect a failure of detection of a lesion site by the user or the detection processing by comparing the first capturing time with the second capturing time.

8. The information processing device according to claim 1, wherein the detection processing is by using optimized machine learning model.

9. A display method comprising:
   acquiring a first capturing time and a first lesion image of a lesion image instructed to be saved by a user, from a series of images captured by an endoscope during examination with the endoscope;
   acquiring a second capturing time and a second lesion image of a lesion image detected by detection processing for the series of images captured by the endoscope during the examination;
   performing control so as to display the first lesion image in association with the first capturing time, and display the second lesion image in association with the second capturing time;
   displaying a position in the second lesion image of a lesion site detected by the detection processing; and
   based on an instruction to select the first lesion image or the second lesion image input from the user and detection failure information of the selected lesion image input from the user, generating feedback data in which the lesion image and the detection failure information are associated with each other, the feedback data being data for improving detection accuracy of the detection processing, wherein
   the detection failure information includes information indicating the lesion image depicted with a lesion detected by the user although the detection is overlooked by the detection processing.

10. A non-transitory computer-readable medium storing a program that causes a computer to execute:
   a first acquisition step of acquiring a first capturing time and a first lesion image of a lesion image instructed to be saved by a user, from a series of images captured by an endoscope during examination with the endoscope;
   a second acquisition step of acquiring a second capturing time and a second lesion image of a lesion image detected by detection processing for the series of images captured by the endoscope during the examination;
   a display control step of performing control so as to display the first lesion image in association with the first capturing time, and display the second lesion image in association with the second capturing time;
   a display control step of displaying a position in the second lesion image of a lesion site detected by the detection processing; and
   a generation step of, based on an instruction to select the first lesion image or the second lesion image input from the user and detection failure information of the selected lesion image input from the user, generating feedback data in which the lesion image and the detection failure information are associated with each other, the feedback data being data for improving detection accuracy of the detection processing, wherein
   the detection failure information includes information indicating the lesion image depicted with a lesion detected by the user although the detection is overlooked by the detection processing.

* * * * *